United States Patent
Sackellares et al.

(10) Patent No.: US 10,849,563 B2
(45) Date of Patent: Dec. 1, 2020

(54) METHODS AND SYSTEMS FOR BRAIN FUNCTION ANALYSIS

(71) Applicant: University of Florida Research Foundation, Inc., Gainesville, FL (US)

(72) Inventors: James Chris Sackellares, Gainesville, FL (US); Scott T. Bearden, Waldo, FL (US); Panagote M. Pardalos, Gainesville, FL (US); Jui-Hong Chien, Baltimore, MD (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 608 days.

(21) Appl. No.: 14/386,643

(22) PCT Filed: Mar. 6, 2013

(86) PCT No.: PCT/US2013/029293
§ 371 (c)(1),
(2) Date: Sep. 19, 2014

(87) PCT Pub. No.: WO2013/142051
PCT Pub. Date: Sep. 26, 2013

(65) Prior Publication Data
US 2015/0088024 A1    Mar. 26, 2015

Related U.S. Application Data

(60) Provisional application No. 61/612,647, filed on Mar. 19, 2012.

(51) Int. Cl.
*A61B 5/00* (2006.01)
*A61B 5/0476* (2006.01)
(Continued)

(52) U.S. Cl.
CPC ........ *A61B 5/7214* (2013.01); *A61B 5/04012* (2013.01); *A61B 5/0476* (2013.01);
(Continued)

(58) Field of Classification Search
CPC ..... A61B 5/7214; A61B 5/7475; A61B 5/742; A61B 5/4094; A61B 5/0478;
(Continued)

(56) References Cited

U.S. PATENT DOCUMENTS

| | | | | |
|---|---|---|---|---|
| 5,287,859 A | * | 2/1994 | John | A61B 5/0484 600/544 |
| 5,447,166 A | * | 9/1995 | Gevins | A61B 5/0484 128/925 |

(Continued)

FOREIGN PATENT DOCUMENTS

| | | | | |
|---|---|---|---|---|
| JP | 2003-159225 A | * | 6/2003 | ........... A61B 5/0478 |
| WO | WO2007/016149 | | 2/2007 | |

OTHER PUBLICATIONS

Horstmann et al., State dependent properties of epileptic brain networks: Comparative graph—theoretical analyses of simultaneously recorded EEG and MEG, Clinical Neurophysiology 121 (2010) 172-185.*

(Continued)

*Primary Examiner* — Jacqueline Cheng
*Assistant Examiner* — Tho Q Tran
(74) *Attorney, Agent, or Firm* — Thomas Horstemeyer, LLP

(57) ABSTRACT

Various methods and systems are provided for cerebral diagnosis. In one example, among others, a method includes obtaining EEG signals from sensors positioned on a subject; conditioning data from the EEG signals to remove artifacts; generating a cerebral network model based at least in part upon the conditioned data; determining network features (Continued)

based upon the cerebral network model; and determining a cerebral condition of the subject based at least in part upon the network features. In another example, a method includes determining a recording condition of a positioned EEG sensor and providing an indication of an unacceptable recording condition of the EEG sensor. In another example, a system includes an EEG recording module to acquire signals; a signal conditioning module to condition signal data; a signal analysis module to determine signal features and cerebral network features; and a condition classification module to determine a cerebral condition of the subject.

19 Claims, 19 Drawing Sheets

(51) Int. Cl.
    *A61B 5/04*     (2006.01)
    *A61B 5/0478*     (2006.01)
    *G06K 9/00*     (2006.01)

(52) U.S. Cl.
    CPC .......... *A61B 5/0478* (2013.01); *A61B 5/4094* (2013.01); *A61B 5/7221* (2013.01); *A61B 5/742* (2013.01); *A61B 5/7475* (2013.01); *G06K 9/00523* (2013.01); *G06K 9/00536* (2013.01); *A61B 5/721* (2013.01); *A61B 5/725* (2013.01); *A61B 5/7257* (2013.01)

(58) Field of Classification Search
    CPC . A61B 5/04012; A61B 5/7221; A61B 5/0476; A61B 5/721; A61B 5/7257; A61B 5/725; G06K 9/00536; G06K 9/00523
    See application file for complete search history.

(56) References Cited

U.S. PATENT DOCUMENTS

| | | | | |
|---|---|---|---|---|
| 7,433,732 | B1* | 10/2008 | Carney | A61B 5/0476 600/544 |
| 2003/0171685 | A1* | 9/2003 | Lesser | A61F 7/12 600/509 |
| 2004/0248802 | A1* | 12/2004 | Eisenbach-Schwartz | A61K 38/02 514/8.3 |
| 2008/0183097 | A1* | 7/2008 | Leyde | A61B 5/0006 600/545 |
| 2009/0082689 | A1 | 3/2009 | Guttag et al. | |
| 2009/0082690 | A1* | 3/2009 | Phillips | A61N 2/12 600/544 |
| 2009/0124923 | A1* | 5/2009 | Sackellares | A61B 5/048 600/544 |
| 2009/0259137 | A1 | 10/2009 | Delic et al. | |
| 2011/0224569 | A1 | 9/2011 | Isenhart et al. | |
| 2011/0307030 | A1* | 12/2011 | John | A61N 1/36017 607/45 |
| 2012/0003862 | A1 | 1/2012 | Newman et al. | |
| 2012/0265262 | A1* | 10/2012 | Osorio | A61N 1/36114 607/3 |
| 2013/0274625 | A1* | 10/2013 | Sarma | A61B 5/048 600/544 |

OTHER PUBLICATIONS

Morgan et al., Nonrandom connectivity of the epileptic dentate gyrus predicts a major role for neuronal hubs in seizures, PNAS, Apr. 2008, 6179-6184.*
Sporns et al., Identification and Classification of Hubs in Brain Networks, PLOS One, Oct. 17, 2007.*
Andreas A Ioannides, Dynamic functional connectivity, Current Opinion in Neurobiology, vol. 17, pp. 161-170 (Year: 2007).*
Ahamdlou et al. (Functional community analysis of brain: A new approach for EEG-based investigation of the brain pathology, NeuroImage 58 (2011) 401-408) (Year: 2011).*
Abdulhamit Subasi "EEG Signal Classification using Wavelet Feature Extraction and a Mixture of Expert Model"; Expert Systems With Applications, vol. 32, Issue 4, May 31, 2007, pp. 1084-1093.
Supplemental search report and written opinion from related EP application No. 13764042.1 dated Oct. 23, 2015.
Willem De Haan et al., Functional neural network analysis in frontotemporal dementia and Alzheimer's disease using EEG and graph theory, BMC Neuroscience 2009, 10:101, http://www.biomedcentral.com/1471-2202/10/101.
Jiang Zheng-Yan, et al., Abnormal cortical functional connections in Alzheimer's disease: analysis of inter- and intra-hemispheric EEG coherence*, Jiang / J Zhejiang Univ SCI 2005 6B(4):259-26.

* cited by examiner

METHODS AND SYSTEMS FOR BRAIN FUNCTION ANALYSIS

CROSS REFERENCE TO RELATED APPLICATIONS

This application is the 35 U.S.C. § 371 national stage of PCT Application No. PCT/US2013/029293, filed Mar. 6, 2013, which is entirely incorporated herein by reference and which also claims priority to, and the benefit of, U.S. provisional application entitled "METHODS AND SYSTEMS FOR BRAIN FUNCTION ANALYSIS" having Ser. No. 61/612,647, filed on Mar. 19, 2012, which is entirely incorporated herein by reference.

BACKGROUND

The human brain is a very delicate organ that makes possible complex behavioral decision making. Information processing within the human brain is so sophisticated and complex that it cannot be accessed entirely even with the advanced technology available today. Once a brain is damaged, it is often very hard to achieve full recovery. The importance of accurate, timely diagnoses of brain abnormality is crucial in many clinical settings including the emergency room (ER) or intensive care unit (ICU). However, most mental and neurological states are evaluated mainly through interviews and subjective exams based on the subjects' temporary performance at that time. There is no objective quantitative test for evaluating baseline brain function. Imaging technologies such as standard magnetic resonance imaging (MRI) show only structure within the brain without providing an indication of dynamic brain function. EEG is the most effective method for evaluating brain function, but interpretation requires interpretation of multichannel graphs based on visual analysis by highly trained experts.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
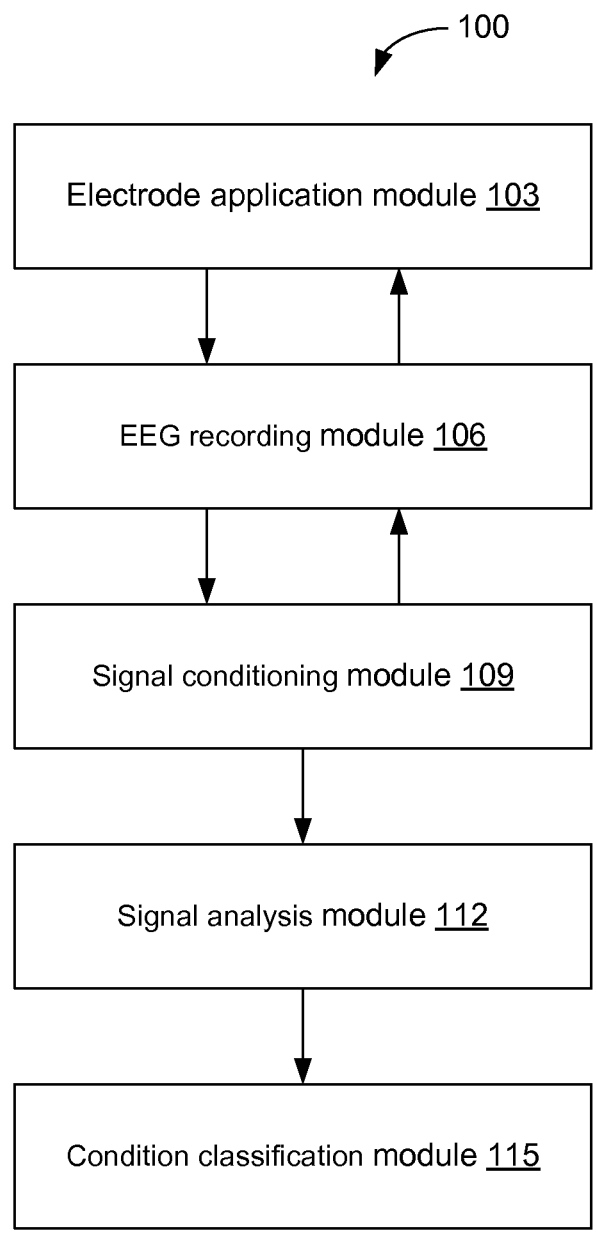
FIG. 1 is a block diagram illustrating an example of a system for evaluating a condition of a brain in accordance with various embodiments of the present disclosure.

Disclosed herein are various embodiments of methods and systems related to diagnosis of cerebral conditions which cause disturbances in brain function. Reference will now be made in detail to the description of the embodiments as illustrated in the drawings, wherein like reference numbers indicate like parts throughout the several views.

Electroencephalography is a technology for measuring the voltage and frequency of electrical activity from neurons in the cerebral cortex. Electroencephalogram (EEG) electrodes can record brainwaves using electrodes attached to the scalp or, through electrodes placed on the surface of the brain (subdural electrodes) or within brain tissue (depth electrodes) using surgical procedures. A scalp EEG is a non-invasive procedure which provides useful information about brain state and function. This methodology is used in many fields of neuroscience (e.g., psychology, epilepsy, brain machine interface, and sleep research) for recording and analyzing brain state and function. It is used widely as a diagnostic tool in clinical neurology to evaluate and monitor brain function and to identify disturbances in the function of the brain caused by a variety of insults to the brain, such as concussion, traumatic injury, stroke, tumor, encephalopathies due to toxins or metabolic disturbances and seizures. Many disturbances of brain function can be identified by analysis of brief multichannel EEG recordings using electrodes placed in specific locations on the scalp, based of reference anatomical landmarks. The most widely accepted system of electrode placement is the International 10/20 System of electrode placement. By analyzing the multi-channel EEG data of a short period of time, ongoing background activity can be assessed. Standard routine EEG recordings are approximately 20 minutes in duration. However, background EEG can be assessed with only a few seconds of EEG recording, if the state of the subject is known (e.g., alert, drowsy or light sleep states). A normal brain generates signals with characteristic frequencies, waveforms and spatial organization. Normal brain electrical activity is remarkably symmetrical over the two cerebral hemispheres. In clinical practice, the EEG is analyzed visually to detect diffuse bilaterally disturbances in ongoing background activity as well as focal or lateralized disturbances. This information provides useful diagnostic insight. The EEG is useful for evaluation of chronic conditions, such as dementia. However, its most important use is in the evaluation of acute or subacute conditions presenting as altered mental status or impaired sensorium, such as stupor or coma.

Analysis and interpretation of EEG recordings is performed by experts (usually neurologists with training in the interpretation of EEG recordings) based on visual inspection of multichannel recordings displayed as multichannel graphs of signal voltage over time. The spatial temporal patterns of brain electrical activity can be analyzed though quantitative analysis of the spatial and temporal properties of this activity, generating a mathematical model of the activity, analyzing the properties of the model, and comparing those properties to a standard of norms based on the properties of normal individuals of similar age. A useful mathematical model for analyzing brain state and function is a network model, based on graph theory. Mathematical analysis of local and global properties allow identification of normal physiological states and allow identification of focal, lateralized or diffuse disturbances in physiological function and states. While brief EEG recordings provide useful diagnostic information regarding function and state at the time of recording, analysis of long-term recording is useful for monitoring brain conditions such as level of consciousness, identifying abnormal transients in the signal, such as interictal epileptiform discharges, seizures, acute cerebral ischemia, hypoglycemia or anoxia. Analyzing the spatial-temporal dynamics of long-term EEG recording data can be achieved through use of quantitative dynamical network models. This approach can provide diagnostic information pertaining to the physiological states of the brain, and can be used to identify transient pathological conditions. The above described approach to network analysis of brain electrical activity can be achieved through computer-based algorithms designed to identify artifact, condition the signal, generate quantitative measures of signal properties from each of multiple EEG channels derived from multiple electrodes placed in standard locations on the scalp, generating a network model, calculating local and global properties of the network and comparing to standard network norms derived from normal subjects. These network properties can be monitored over time and compared with the patient or subject's baseline to detect significant changes in state or development of transient pathological conditions. The algorithm can provide detailed quantitative output or can summarize the results and categorize them as normal or abnormal. Abnormalities can be categorized as to focal, lateralized or diffuse, and the anatomical location focal and lateralized abnormalities can be reported. This output can be written as a report or depicted as a graph. The algorithm can be trained and compared to the interpretation of expert electroencephalographers to optimize the sensitivity and specificity of the algorithm. An appendix, which is hereby incorporated by reference in its entirety, provides additional information about EEG analysis of brain dynamical behavior.

This disclosure presents systems and methods for reliably evaluating a recorded EEG in real time by algorithms and providing an immediate indication of the cerebral condition. The acquired EEG data may be evaluated in real time and/or may be stored for subsequent evaluation. The system allows EEG data to be recorded and evaluated when no EEG technical personnel or neurological interpreters are readily available, allowing its use as a screening tool to assist physicians when such personnel are not available. The original EEG data may also be stored for subsequent visual analysis and/or may be transmitted to remote sites for review and interpretation by experts.

EEG data can be recorded with small, portable, inexpensive instruments that do not require special shielded facilities or the subject remaining motionless for long periods of time. Thus, an EEG can be utilized in noisy point-of-care environments, such as Emergency rooms and Intensive Care Units and with subjects who may be uncooperative. Portable EEG units can also be utilized in emergency vehicles and in the field. Referring to FIG. 1, shown is a block diagram illustrating an example of a system 100 for evaluating a condition of a brain. In the embodiment of FIG. 1, the system 100 includes an electrode application module 103, an EEG recording module 106, a signal conditioning module 109, a signal analysis module 112, and a condition classification module 115. The system 100 may contain an interactive display which may provide, e.g., step-by-step instructions on electrode placement, establishing connections, preparing the subject and initiating the recording, etc. The system 100 allows for rapid acquisition and analysis of EEG signals, measurement of the spatial-temporal characteristics of the signal, analysis of local, regional, and diffuse signal characteristics, characterization of network features of EEG signals, determination of whether or not these EEG characteristics are normal or abnormal, and classification of abnormal EEG recordings to determine whether the abnormalities are local, lateralized, multifocal or diffuse. The results may be displayed as in a text and/or graphical format that may be available for immediate use by emergency room personnel, intensive care personnel, and emergency medical technicians.

Figure 2A:
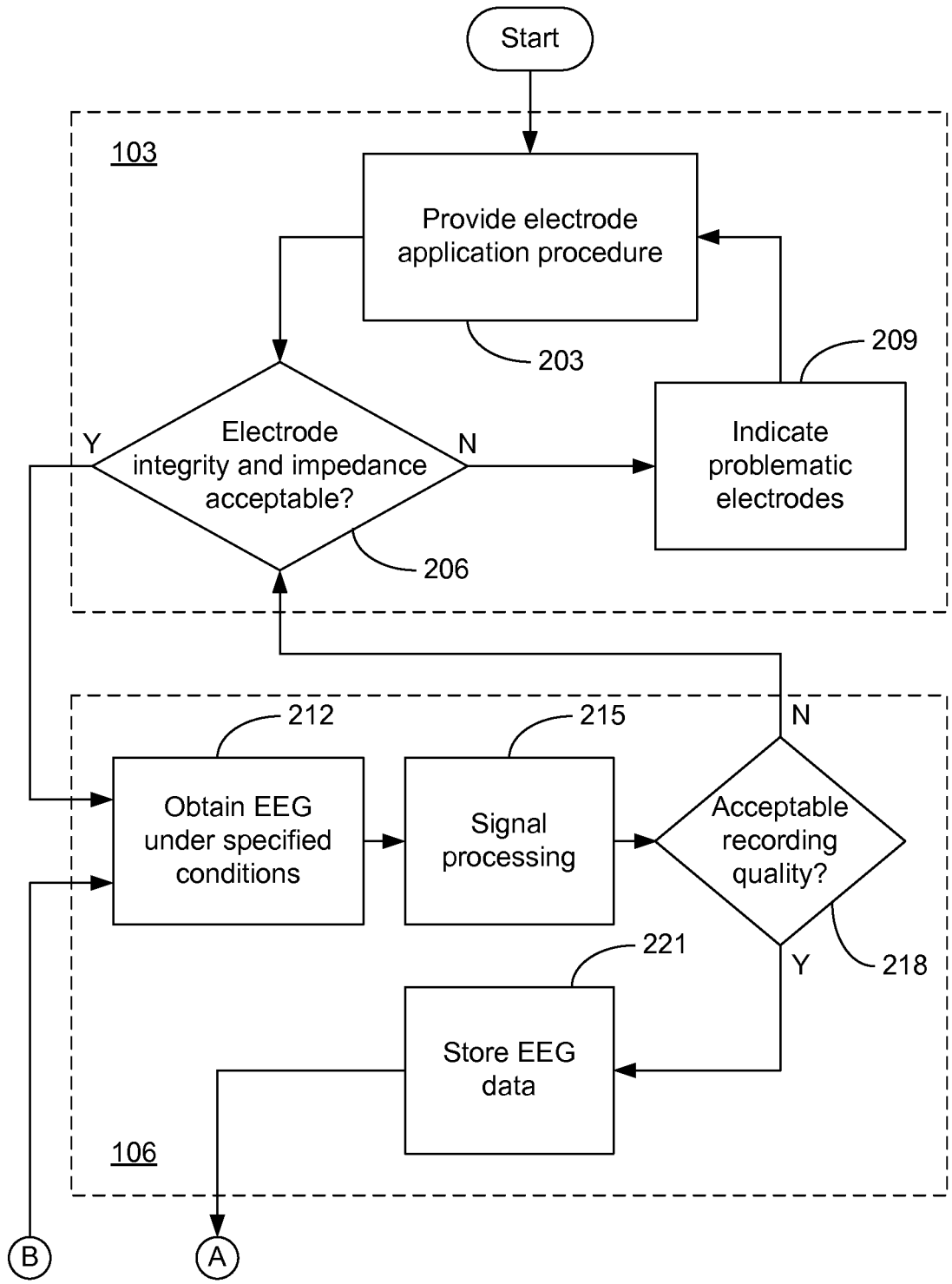
FIGS. 2A and 2B are a flowchart illustrating an example of functionality of the system of FIG. 1 in accordance with various embodiments of the present disclosure.
Figure 2B:
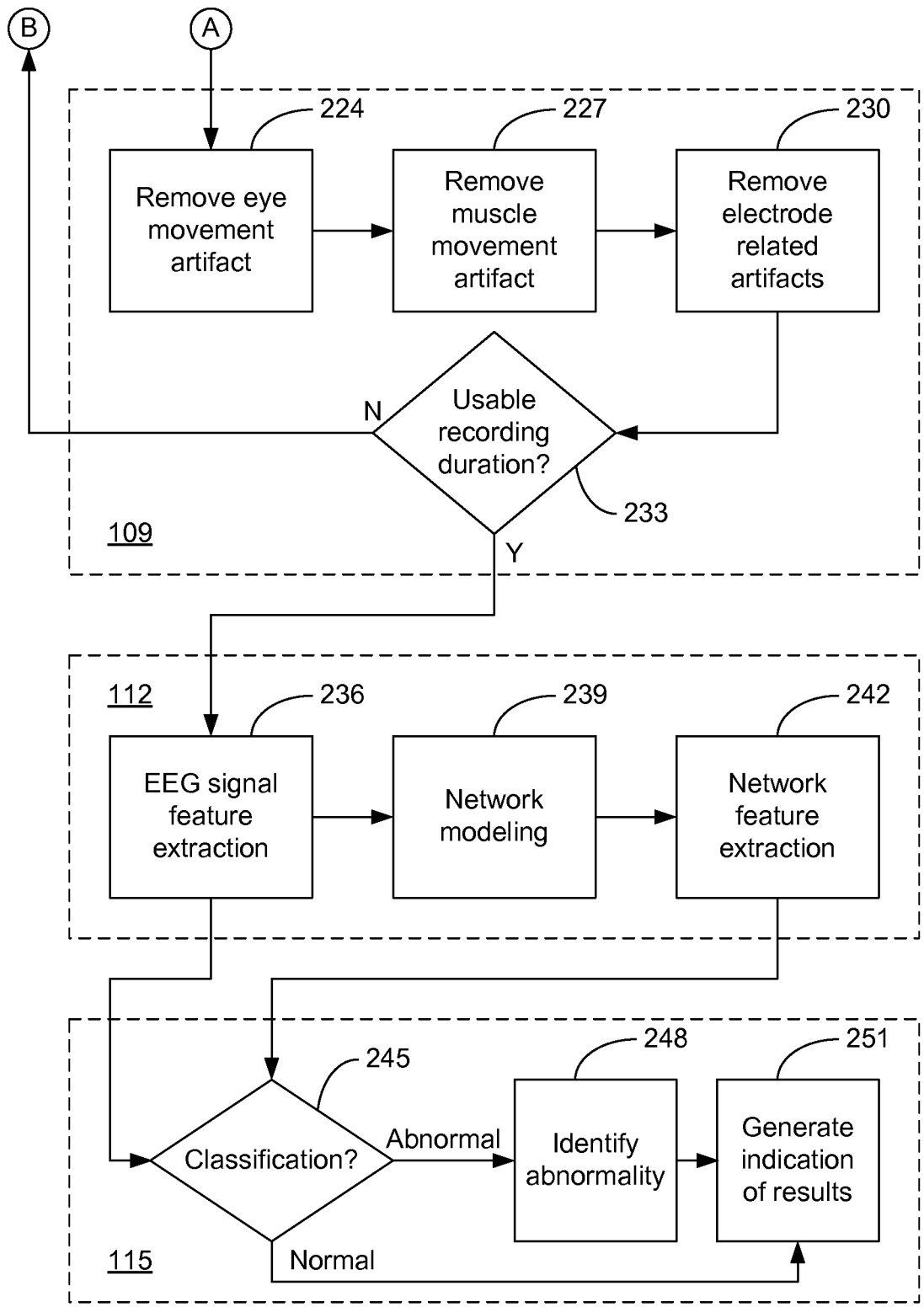

Referring to FIGS. 2A-2B, shown is a flowchart illustrating various functions that may be implemented by modules of the system 100. As shown in FIG. 2A, after operation of the system has been initiated (e.g., by turning on the device), an electrode application procedure may be provided in box 203 by the electrode application module 103 for rendering on the system display. The EEG provides direct information about brain functions through analysis of brain electrical activity. Depending on the location and the type of the electrodes, EEG signals can reveal different levels of neuronal activity. Numerous scalp EEG electrodes may be applied to a subject to obtain EEG data containing information from brain activity in both temporal and spatial domains. The EEG electrodes can include individual electrodes and/or an array of electrodes that are positioned on the scalp. The location of electrode placement on the scalp can follow, e.g., a 10-20 system or other appropriate system as can be appreciated. In the 10-20 system, distinct landmarks of the subject's head are first identified and then electrodes are placed at 10% or 20% distance intervals along the landmarks. In some implementations, intracranial electrodes may be utilized. The recording integrity and impedance of the electrodes are checked in box 206 to determine if there is a problem with the placement and/or operation of the EEG electrodes. If there is a problem, the problematic electrodes may be indicated in box 209 on the system display and the appropriate application or correction procedure(s) may be provided in box 203. Guiding the operator through simple set-up and operating procedures to obtain a technically adequate EEG recording reduces evaluation errors.

If the electrode integrity and impedance is acceptable in box 206, then an EEG is obtained under specified conditions in box 212 by the EEG recording module 106. For example, EEGs may be obtained with the subject's eyes open and closed or other specified conditions of the subject. Instructions may be rendered for display on the system display to prompt the specified condition (or action) in the monitored subject. For example, during a routine EEG examination, a subject is usually asked to relax and open eyes for a period of time and then close eyes for another period of time. The acquired EEG signals are then processed in box 215. For example, amplification and filtering may be applied to enhance the signal-to-noise ratio (SNR) of the EEG signals. Analog EEG signals from the electrodes may also be digitized for communication and storage of the information. In box 218, acceptability of the recording quality of the EEG data is confirmed. For example, all channels of the processed EEG signal may be analyzed for the presence of excessive artifacts that may contaminate the EEG data. Criteria for acceptable signal quality may be predefined to ensure acceptable electrode contact, electrode impedance, and minimal contamination by common artifacts.

If the EEG data is not acceptable, then the system can return to box 206 to recheck electrode integrity and impedance. Common technical problems that degrade the recording (e.g., excess muscle or movement artifacts) may also be determined in box 218. Instructions may be provided through the system display to guide the operator in methods to eliminate or attenuate those artifacts before repeating the acquisition of EEG signals in box 212. Subsequent recorded EEG data may be re-evaluated and the operator notified of persistent problems, at which time the operator may attempt to obtain further EEG signals or may abort the procedure. If the EEG data is acceptable, the digitized data can be stored in a data store or other memory in box 221. The stored EEG data may be transmitted through a wireless or wired network connection (e.g., cellular, Bluetooth, Ethernet, etc.) for remote evaluation, analysis, and/or confirmation.

The acceptable EEG data is further processed and/or filtered by the signal conditioning module 109 to remove common recording artifacts as illustrated in FIG. 2B. For example, eye movement artifacts may be detected and removed in box 224, electromyogram (muscle movement) artifacts may be detected and removed in box 227, and electrode related artifacts such as, e.g., electromagnetic interference from nearby instruments may be detected and removed in box 230. Other artifacts such as, e.g., 60 Hz line signals and signals produced by mechanical ventilators and other instruments may also be detected and removed from the EEG data by the signal conditioning module 109. For example, epochs of data may be examined sequentially for the presence of an artifact. If a segment contains an excessive artifact, it may then be excluded from subsequent analysis. After the signal conditioning module 109 identifies and discards the artifact-contaminated segments, the remaining EEG data is evaluated in box 233 to ensure that a useable signal of sufficient duration has been acquired and is available for analysis. An initial interpretation may be generated based upon a brief EEG recording (e.g., 2 to 5 minutes). If the available data is not long enough for reliable analysis, the system 100 will inform the operator and return to box 212 to obtain additional EEG data. If the available EEG data is long enough for analysis or evaluation, the EEG data is processed by the signal analysis module 112 to extract features in box 236.

The system 100 may also provide an option to continue recording to obtain a complete routine EEG (typically around 20-30 minutes of recording) or for continued monitoring the EEG for changes in brain function, such as intermittent seizures, diffuse or focal ischemia, and changes in alertness or level of consciousness. In other implementaions, the system 100 may be placed in a monitoring mode in which epochs of the EEG are analyzed as they are acquired to detect transient abnormalities or state changes in the subject. In the monitoring mode, a continuous or intermittent analysis may be provided graphically and/or a summary report may be provided intermittently at specified intervals. For example, the interval between reports can be a default interval (e.g., every 10 minutes) or can be an interval that is selected by the operator.

The extracted features of the multichannel EEG data from box 236 may be used to provide a quantitative description of the spatiotemporal characteristics of the signals, including local and regional characteristics, inter-hemispheric asymmetries, and local and global network connectivity characteristics. The extracted features may be, e.g., linear, non-linear, univariate, or bivariate statistics. The extracted features from box 236 may be provided as inputs for network modeling in box 239 and for classification of the cerebral condition in box 245 of the condition classification module 115. For example, if the feature is univariate, such as entropy, each EEG channel will have a feature time series. The network modeling in box 239 is implemented based upon the degree of association between these univariate features between channels. If the feature is bivariate (or a relationship between two channels), the network modeling in box 239 may be directly implemented through the values of bivariate features. After the network model has been constructed in box 239, network features may be extracted in box 242 from the network model and provided to the condition classification module 115 for classification in box 245. Classification of the cerebral condition can be more precise by including the extracted network features in the evaluation.

Classification of the cerebral condition in box 245 may be based, at least in part, upon comparison of extracted features from boxes 236 and 242 by comparison with established norms to determine if they indicate a normal condition within normal limits or an abnormal condition. In addition being able to utilize correlations between specific EEG findings and pathologies, the condition classification module 115 analyzes EEG signals through a network perspective. The functional network reflects the connectedness among brain regions in terms of neuron activity. The brain functional network may be represented as a graph by defining vertices and edges in the EEG data. If the EEG channels are designated as the vertices of a graph, an edge between two vertices signifies a functional connection between two EEG channels. A larger correlation between two EEG channels indicates the presence of an edge between the channels. Edges may also be values quantifying how well the two vertices correlate in weighted graphs. Applying graph theoretical analysis to EEG data can reveal topological characteristics of the neural network and brain functional network features.

If the cerebral condition is determined to be abnormal, then the location of abnormal features (e.g., local or focal, lateralized, or diffuse bilateral) and/or the severity of the abnormality (e.g., mild, moderate, or severe) may be identified in box 248. For example, the condition may be identified as abnormal diffuse bilateral, abnormal left hemisphere, or abnormal right hemisphere with slowing, seizures, and/or amplitude disturbance. An indication of the classification results may then be generated in box 251 for rendering on the system display. For example, a graphic display of the original EEG signal, local signal properties, inter-hemispheric asymmetries, local network features, and/ or global network features may be generated. A warning may be generated when an abnormal condition has been indicated.

A summary (or report) of findings may be provided in several forms which may be selected by the user. For example, a default condition may provide a report labeled as normal or indicating the determined abnormal category classification (e.g., mildly abnormal, left hemisphere). In addition, a visual display of the anatomical location of the abnormalities may be provided graphically, using a color bar, grey scale or other graphic display to indicate the severity of the abnormalities. Other graphical displays which provide maps of one or more individual signal property may also be viewed. The results of the classifications may also be stored in box 251 for later access or retrieval to further evaluation, interpretations, and validation.

Figure 3A:
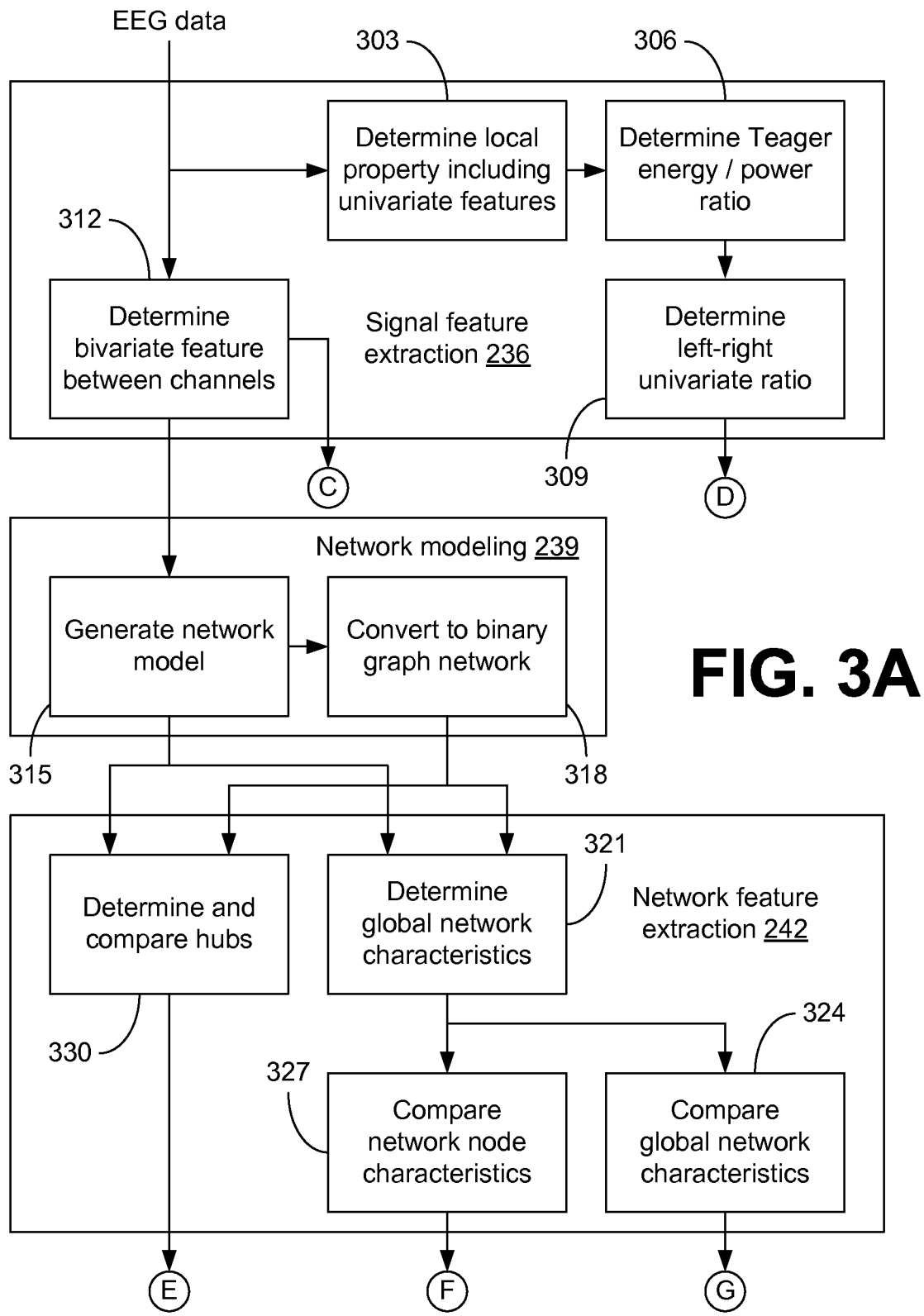
FIGS. 3A and 3B are a flowchart illustrating examples of feature extraction, network modeling, and classification of the flowchart of FIG. 2B in accordance with various embodiments of the present disclosure.

Referring to FIGS. 3A and 36, shown are a flowchart illustrating examples of feature extraction, network modeling, and classification of the flowchart of FIG. 2B. In FIG. 3A, EEG data is received for EEG signal feature extraction in box 236. In box 303, local properties may be determined from the EEG data including the univariate feature. Kaiser-Teager energy and power in the EEG may be computed for each electrode site and referenced to a common reference electrode (e.g., average, Pz, other). Other implementations may use bipolar pairs and calculate for each pair: Fp1-F3, F3-C3, C3-P3, P3-O1 and analogous for right side, Fp1-F7, F7-T3, T3-T5, T5, O1 and analogous for right side.

Local energy and power properties may be determined for each channel for comparison to predetermined normative values for each channel. Abnormality of Teager energy and abnormalities for power would be expected to be either higher or lower than the normative values. Abnormalities in the Teager energy to Power ration would be expected to be lower than norms. Norms may be derived from EEG recordings obtained from a normal test group, with appropriate age matching, or may be based upon baseline recordings obtained in the same subject (in which case, a change from baseline would be detected).

For each EEG channel, the follow local property values may be computed in box 303:

Kaiser-Teager energy (KTE). KTE may be calculated for each electrode channel. This value can be obtained for the entire recorded frequency range as well as for each of the standard EEG frequency bands (delta: 0-4 Hz, theta: 4-8 Hz, alpha: 8-13 Hz, and beta: 13-30 Hz). The value for each channel may be compared to normal values. If the values are outside of the normal range, the degree of abnormality (e.g., based on standard deviations (s.d.) from the mean) for each electrode channel can be determined. The location (left cerebral hemisphere, right cerebral hemisphere or bilateral) and degree of abnormality (1 s.d.$\geq$x<2 s.d., 2 s.d.$\leq$x$\leq$3 s.d, or x$\geq$3 s.d.) can be stored and used in the final evaluation and report.

Power. Standard power for the entire frequency range (0 to 30 Hz) and for each of the standard EEG frequency bands (delta, theta, alpha and beta) may be computed for each electrode channel and compared to normal values for each respective channel. If the values are outside of the normal range, the degree of abnormality (based on standard deviations from the mean) for each electrode channel can be determined. The location (left cerebral hemisphere, right cerebral hemisphere or bilateral) and degree of abnormality (1 s.d.$\geq$x<2 s.d., 2 s.d.$\leq$x<3 s.d, or x$\geq$3 s.d.) can be stored and used in the final evaluation and report.

Pattern match regularity statistic (PMRS). One or more measures of signal regularity or signal such as the PMRS may be generated for the entire recorded frequency range as well as for each standard EEG frequency band for each electrode channel and compared to normal values. If the values are outside of the normal range, the degree of abnormality (based on standard deviations from the mean) for each electrode channel can be determined. The location (left cerebral hemisphere, right cerebral hemisphere or bilateral) and degree of abnormality (1 s.d.$\geq$x<2 s.d., 2 s.d.$\leq$x<3 s.d, or x$\geq$3 s.d.) can be stored and used in the final evaluation and report.

Approximate entropy. One or more measures of signal entropy, such as approximate entropy, may be measured for the entire recorded EEG frequency range as well as for each of the standard EEG frequency bands for each electrode channel and compared to normal values. If the values are outside of the normal range, the degree of abnormality (based on standard deviations from the mean) for each electrode channel can be determined. The location (left cerebral hemisphere, right cerebral hemisphere or bilateral) and degree of abnormality (1 s.d.$\geq$x<2 s.d., 2 s.d.$\leq$x<3 s.d, or x$\geq$3 s.d.) can be stored and used in the final evaluation and report.

Teager energy/power ratios are generated for each channel for entire frequency range between 1 and 30 Hz in box 306. For each EEG channel, the KTE to power ratio may be calculated for the entire recorded frequency range as well as for the standard EEG frequency bands is calculated for each channel and compared to normal values. If the values are outside of the normal range, the degree of abnormality (based on standard deviations from the mean) for each electrode channel can determined. The location (left cerebral hemisphere, right cerebral hemisphere or bilateral) and degree of abnormality (1 s.d.$\geq$x<2 s.d., 2 s.d.$\leq$x<3 s.d, or x$\geq$3 s.d.) can be stored and used in the final evaluation and report.

Left-right univariate ratios may then be determined in box 309. Inter-hemispheric symmetry computation may be based upon univariate features. Each of the quantitated measures of signal properties, such as those described above, will be examined for inter-hemispheric symmetry by calculating the ration of the value obtained for each of the electrode channels recorded from the left cerebral hemisphere to the same value obtained for the homologous electrode channel in the right hemisphere.

In box 312, bivariate features between all channels may also be determined from the EEG data. Inter-hemispheric symmetry computations may be based upon bivariate features. Bivariate measures can be used to evaluate the relationship of signals obtained from each electrode channel from the left cerebral hemisphere to that of the homologous electrodes from the right cerebral hemisphere. These measures include mutual information, linear or nonlinear correlation, coherence, phase locking index and phase lag index. The analysis can be made for the entire range of recorded frequencies as well as for each standard EEG frequency band.

A network model may then be generated in box 315 based upon the bivariate feature values from box 312. A network model can be generated as a weighted graph, based on one or more of the bivariate measures relating signal properties between each pair of electrodes, such that a measure is generated for each electrode site (node) and all other electrodes in the recording. The weighted graph can be converted to a binary graph depicting the node pairs with the strongest association, as defined by one or more bivariate measure, using a threshold in box 318. For example, a threshold of 0.75 may be used, such that the resultant binary graph includes 25% of the total electrode pairs; in the case of a full set of electrodes, excluding midline electrodes, as defined by the International 10-20 System of electrode placement, the total number of pairs is 171 and 43 pairs would be selected for the binary network graph.

In box 321, global network characteristics of the binary and/or weighted network graphs may be determined. These characteristics include, e.g., clustering coefficient and minimum path length. These global characteristic values are compared to norms in box 324 to determine whether or not they are within the normal range. If the values are outside of the normal range, the degree of abnormality (based on standard deviations from the mean) for each electrode channel is determined. The location (left cerebral hemisphere, right cerebral hemisphere or bilateral) and degree of abnormality (1 s.d.$\geq$x<2 s.d., 2 s.d.$\leq$x<3 s.d, or x$\geq$3 s.d.) will be stored and used in the final evaluation and report.

In addition, characteristics for each node (or electrode) can be defined, based on the following characteristics for each node: degree, path length to contralateral homologous electrode, and connection strength with contralateral homologous electrode. For each electrode, the degree of that node can be compared to the degree for the same electrode (node) in the normative dataset in box 327 and the location of nodes whose properties do not match those of the normative dataset can be determined.

In box 330, hubs of the binary and/or weighted network graphs may be identified using one or more criteria for defining hubs, such as degree, betweeness, closeness, and eigen vector centrality. Electrodes which exceed thresholds of the values for each respective measure can be defined as a network hub. Network hubs identified in the recording can be compared to a list of hubs obtained from a normative comparison dataset. Hubs present in the subject network which do not correspond to hubs in the normal datasets may be identified and their location determined to be lateralized to one cerebral hemisphere, localized within one cerebral, or present bilaterally. In addition, nodes in the recorded data which are not present in the normative datasets can be identified and localized. In a similar fashion, the path length between each electrode (node) and the homologous node in the contralateral hemisphere may be calculated. Values for each channel pair can be compared to those of the normal dataset and the location of those pairs which differ significantly from the normal datasets can be determined.

Figure 3B:
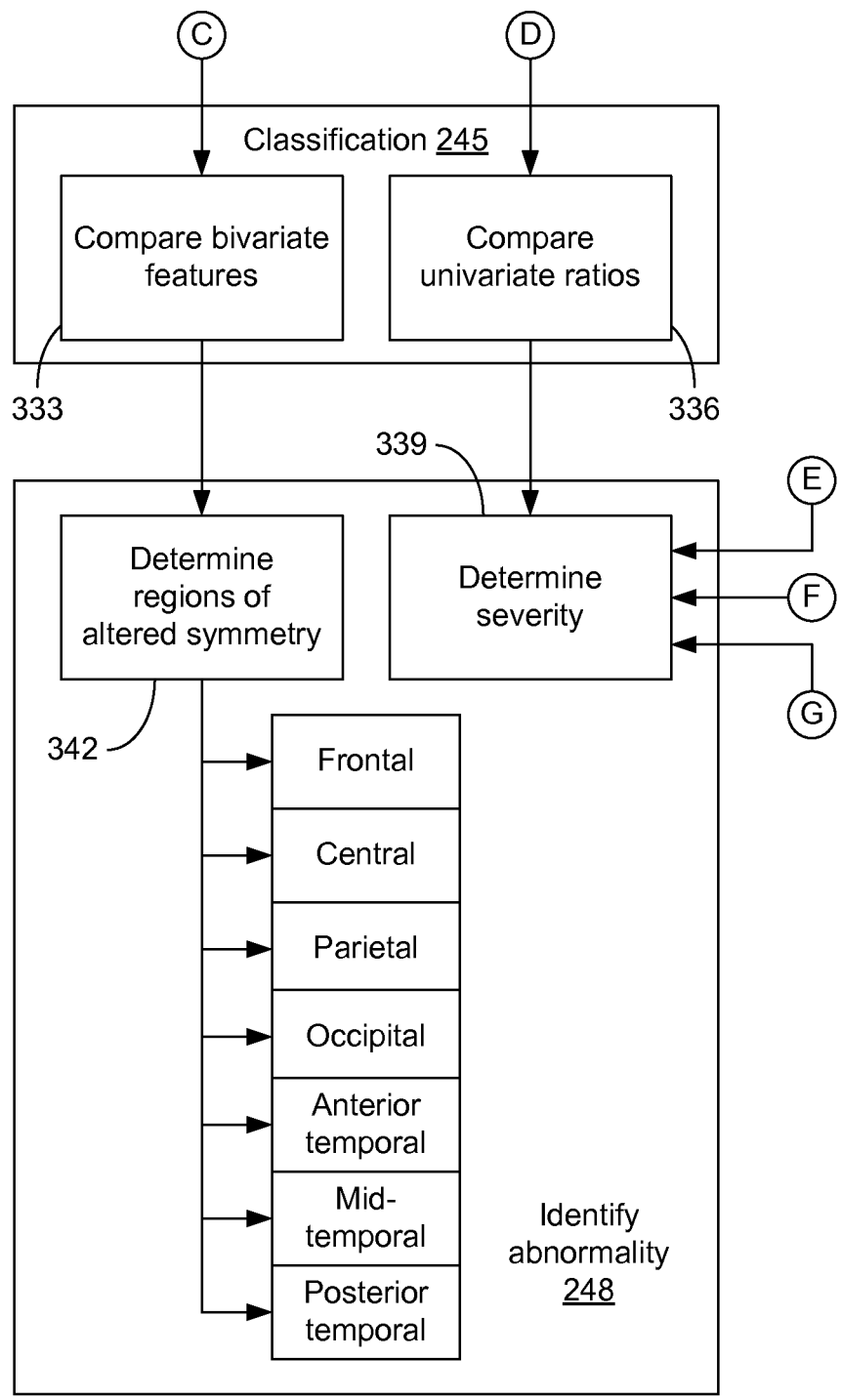

The cerebral condition can be classified in box 245 of FIG. 3B based upon comparison of values from boxes 309 and 312 of FIG. 3A. After signals have been analyzed and results stored, the EEG data may be classified, based on the composite results from all, or a subset, of each individual analysis: (1) local univiariate signal properties, (2) inter-hemispheric symmetry computations based on local univariate signal properties, (3) inter-hemispheric symmetry based on computations of biviariate signal properties, local network properties, and global network properties. If all of these analyses are within acceptable range of normal values, the recording may be classified as normal.

In box 333, the bivariate feature of homologous pairs is compared with normal values obtained from the same electrode pairs. If the values are outside of the normal range, the degree of abnormality (based on standard deviations from the mean) for each electrode channel may be determined. The location (left cerebral hemisphere, right cerebral hemisphere or bilateral) and degree of abnormality (1 s.d.$\geq$x<2 s.d., 2 s.d.$\leq$x<3 s.d, or x$\geq$3 s.d.) can be stored and used in the final evaluation and report. In box 336 of FIG. 3B, univariate ratios from each channel pair will be compared to normal ratios for that channel pair. If the ratios are outside of the normal range, the degree of abnormality (based on standard deviations from the mean) for each electrode channel may be determined. The location (left cerebral hemisphere, right cerebral hemisphere or bilateral) and degree of abnormality (1 s.d.$\geq$x<2 s.d., 2 s.d.$\leq$x<3 s.d, or x$\geq$3 s.d.) can be stored and used in the final evaluation and report.

If there are abnormalities identified, the EEG data will be classified as abnormal and assigned to one of several abnormal categories in box 248 of FIG. 3B. For example, the abnormal categories may be defined as follows: (1) left hemisphere abnormality, (2) right hemisphere abnormality, (3) bilateral abnormalities. EEG data with bilateral abnormalities may be further subclassified as (3a) bilateral symmetrical abnormalities, (3b) bilateral abnormalities, left greater than right and (3b) bilateral abnormalities right greater than left. In other implementations, the location of the abnormality may be made more precise, indicating the region(s) within the cerebral hemisphere(s) containing the abnormalities (e.g., left front-temporal abnormality). Abnormal EEG data may be further categorized as to the degree of abnormality, based upon a weighted magnitude of property deviations from normal values as well as the number of properties which deviate significantly from normal values.

In box 342, regions of altered symmetry are identified and the severity determined based upon values from box 333. In addition, the severity of the abnormality is determined in box 339 based upon values for boxes 324, 327, and 330 of FIG. 3A and box 336 of FIG. 3B. As discussed above, the degree of abnormality may be based on standard deviations from the mean the values for each electrode channel. In some cases, a weighed combination of the standard deviations may be used to indicate the degree of abnormality. The results of the abnormality identification may be stored in a data store or memory and may be used to generate an indication for the operator of the system 100.

The system 100 may be used for, but is not limited to, neurological assessment of common neurological presentations such as, e.g., acute encephalopathies, subacute encephalopathies, focal lesions, ischemic events, and chronic encephalopathies. Acute and subacute encephalopathies include such disorders as those due to traumatic brain injuries, toxic encephalopathies (e.g. drug or alcohol toxicity), metabolic disorders (e.g. hypoglycemia, hyperglycemia, ketoacidosis, renal failure, hepatic failure, hypoxia, hypercapnea), acute or subacute infections of the brain (such as meningitis, encephalitis, and brain abscess), seizures, status epilepticus, stroke, transient ischemic attacks, and autoimmune disorders affecting the central nervous system. It may also be used for detecting mild disturbances of brain function including, e.g., concussion following after head injuries. Information obtained through the system 100 may be used to refine the differential diagnosis, formulate further workup (e.g. imaging procedures) and treatment, and for purposes of triage and referral to appropriate facilities and specialists. Other potential uses include brain monitoring to evaluate level of alertness, screening of chronic cerebral disorders such as, e.g., Alzheimer's disease and other chronic dementias, and assessment of excess daytime sleepiness and sleep disorders.

One embodiment, among others, can be an altered mental status evaluator (AMSE). A unique feature of this application is its utility as a tool to assist physicians in the differential diagnosis of subjects in the hospital with acute unexplained persistent altered mental status (AMS). These subjects are commonly seen in the Emergency Room (ER), Intensive Care Unit (ICU) or hospital wards. AMSE provides reliable identification of EEG abnormalities that cause altered mental status including subclinical seizures, diffuse EEG slowing reflecting diffuse encephalopathy and focal EEG slowing reflecting focal brain dysfunction. AMSE then generates a report to assist the physician in diagnosis of subjects with altered mental status. These results can rapidly point the physician to the differential diagnostic areas that should receive the most consideration initially (but should not preclude other avenues of investigation). The physician correlates the results with their clinical examination and results of other studies to reach a final accurate diagnosis more quickly.

Figure 4:
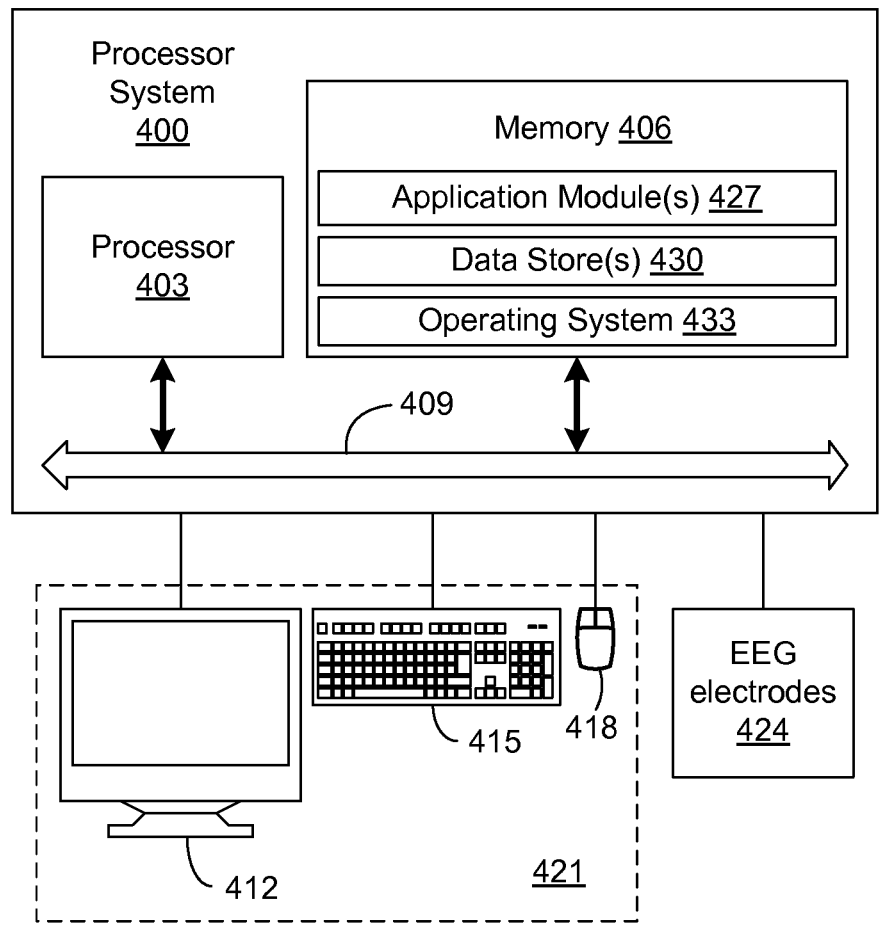
FIG. 4 is a graphical representation of an example of a processor system suitable for implementing the system of FIG. 1 in accordance with various embodiments of the present disclosure.
Figure 5A:
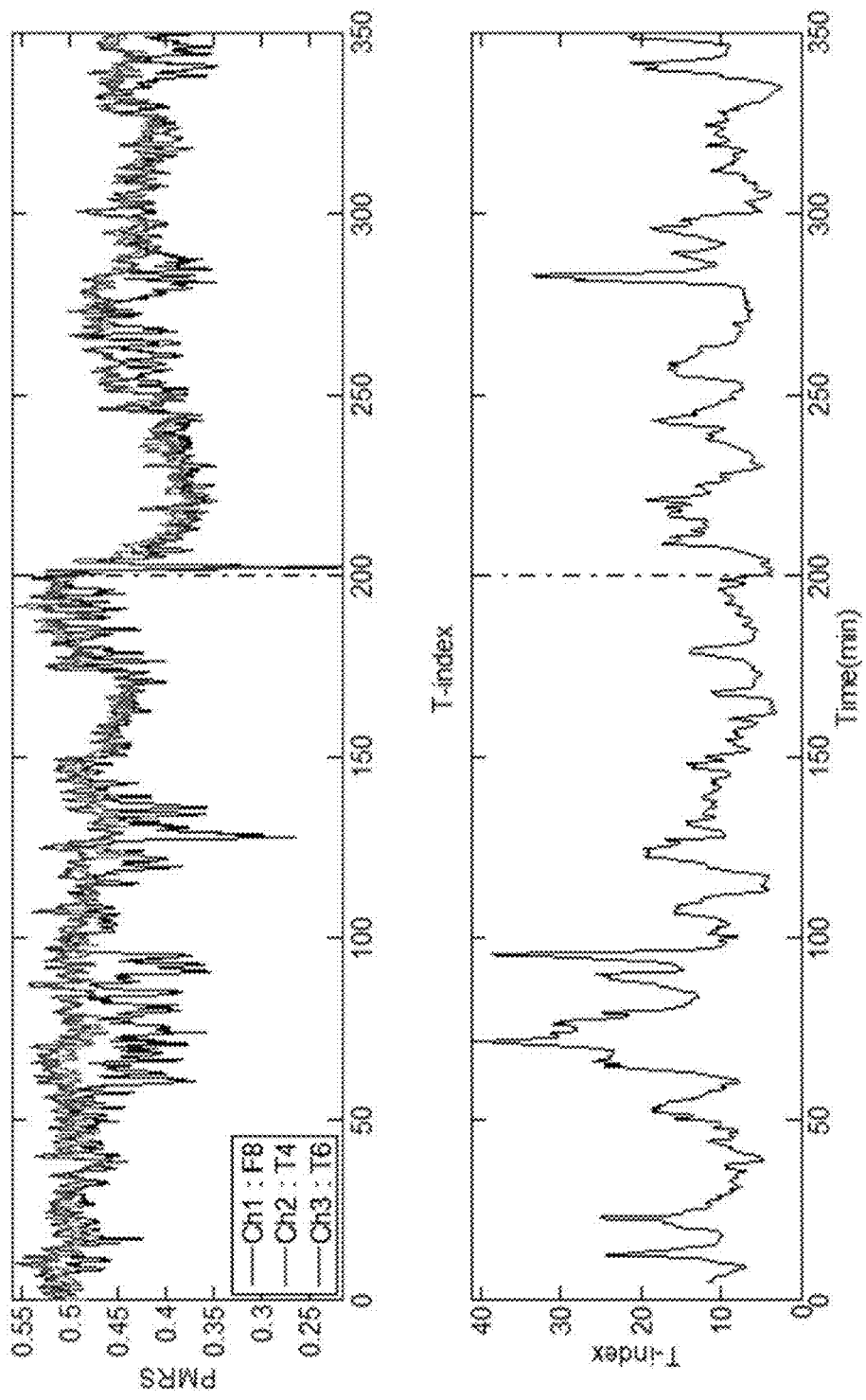
FIG. 5A illustrates dynamic features of three EEG electrode signals.
Figure 5B:
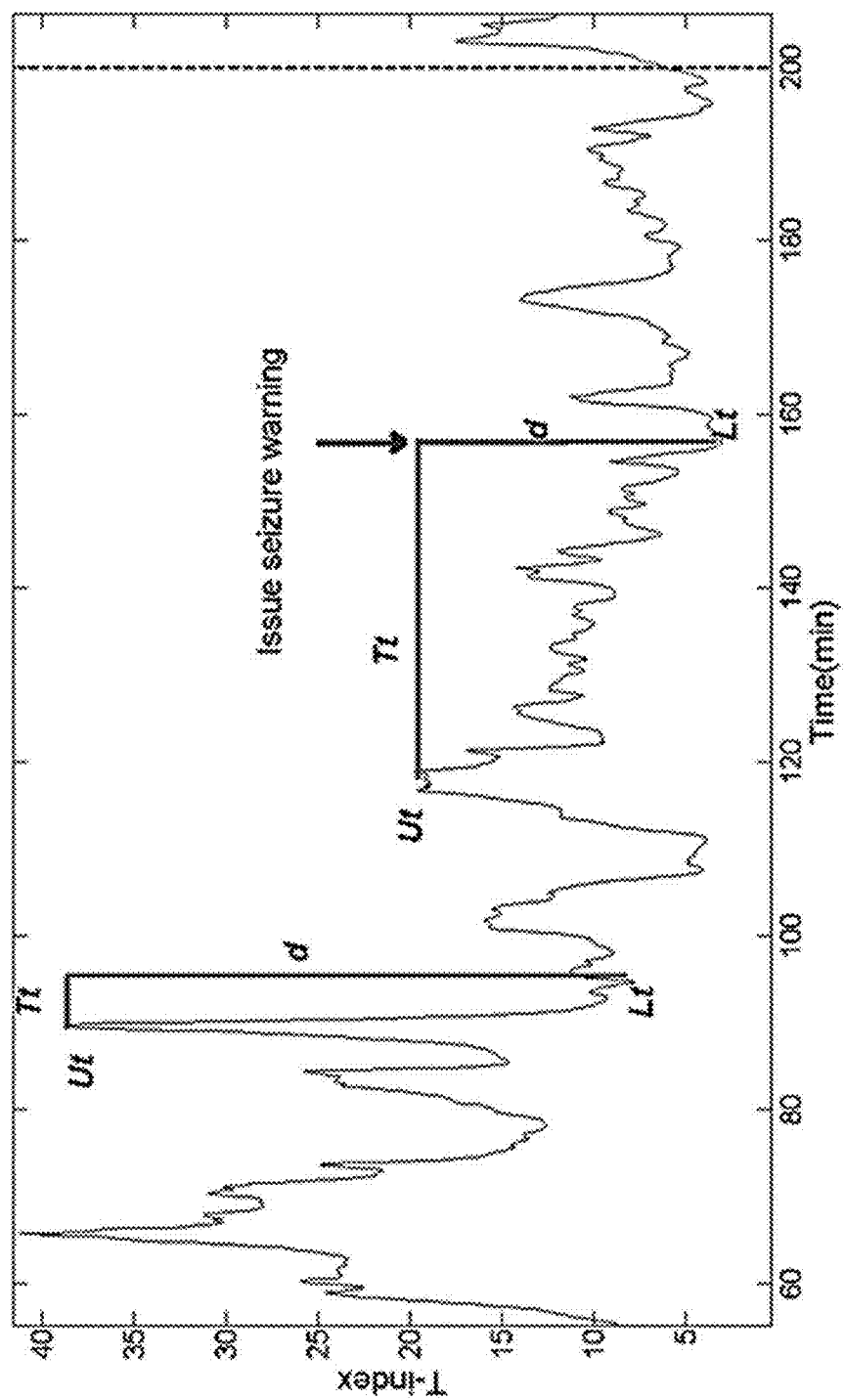
FIG. 5B illustrates a group T-index plot with warning algorithm parameter indications.
Figure 5C:
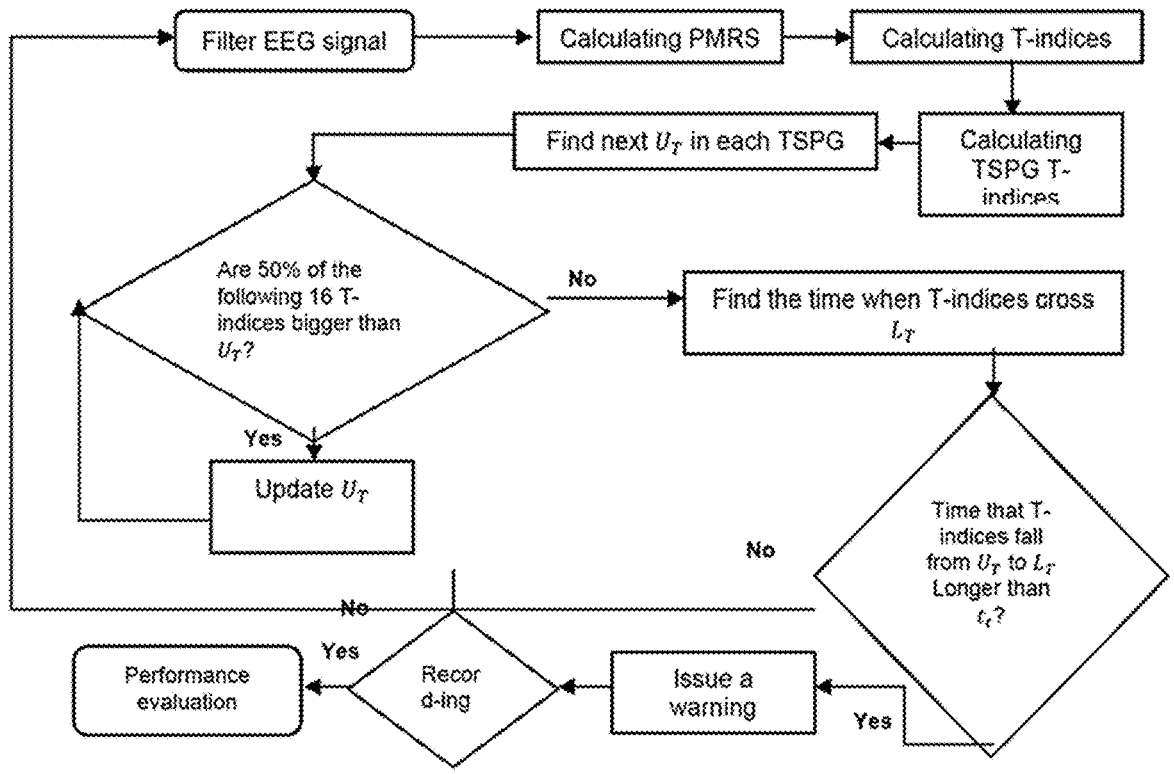
FIG. 5C illustrates a flow chart of the seizure warning mechanism.
Figure 5D:
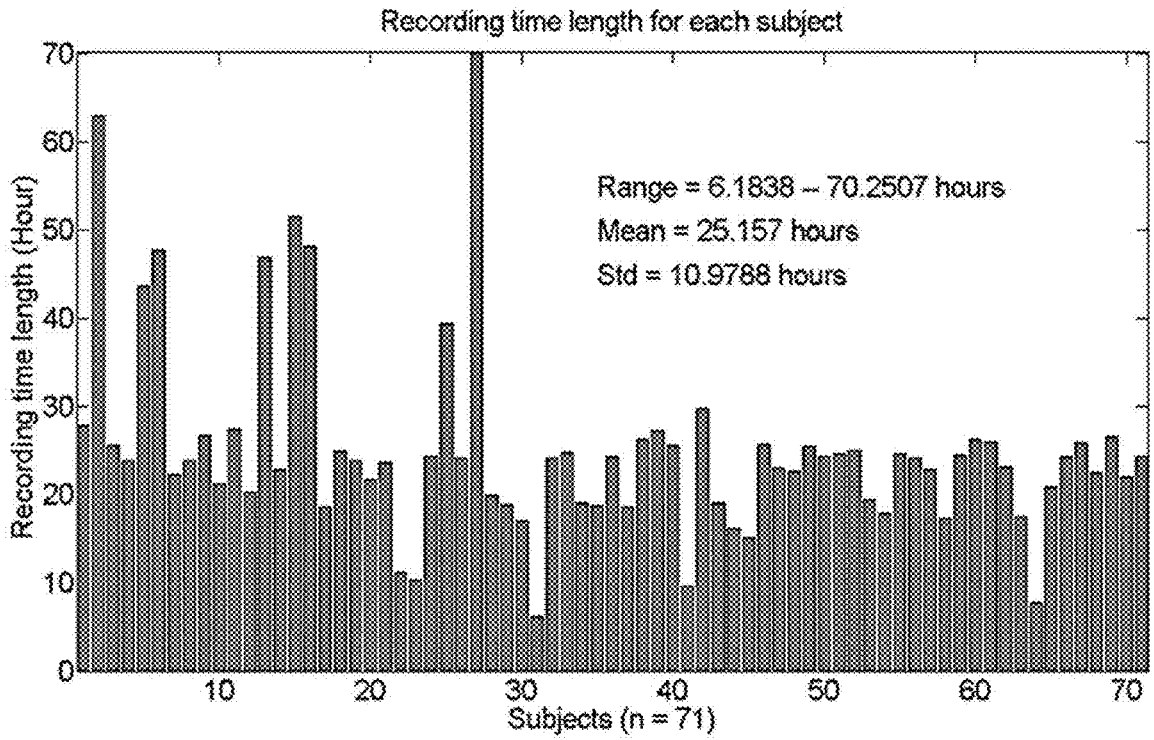
FIG. 5D illustrates recording duration of subjects in the dataset.
Figure 5E:
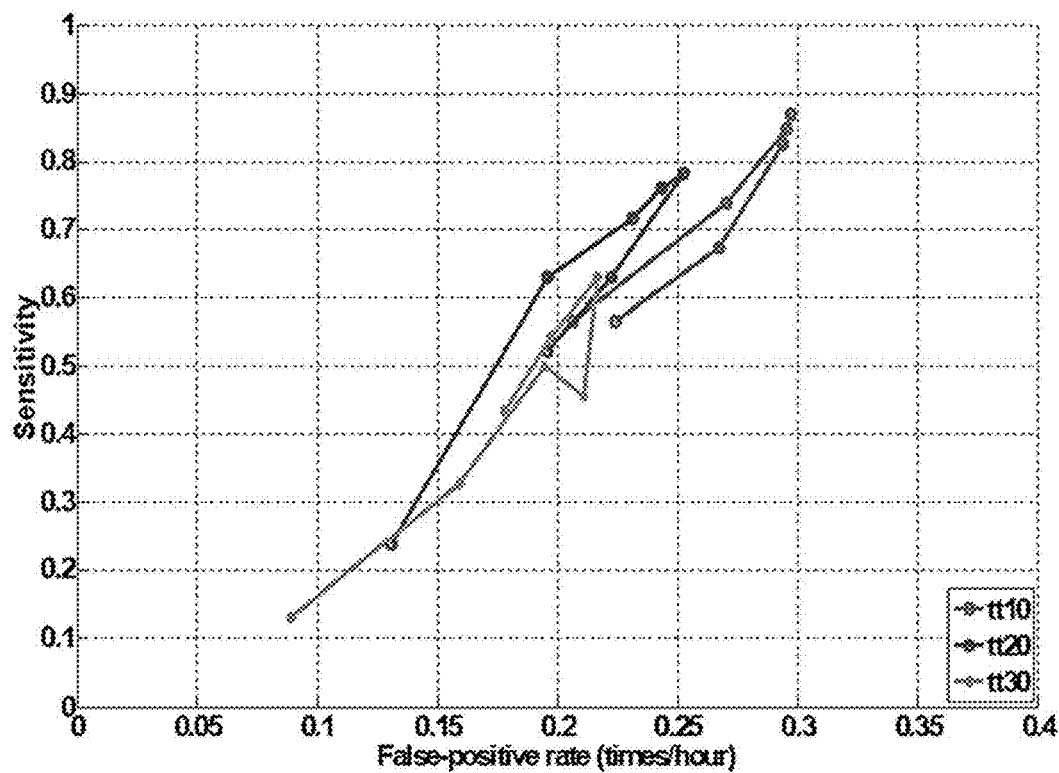
FIG. 5E illustrates a training result from 20 trials.
Figure 5F:
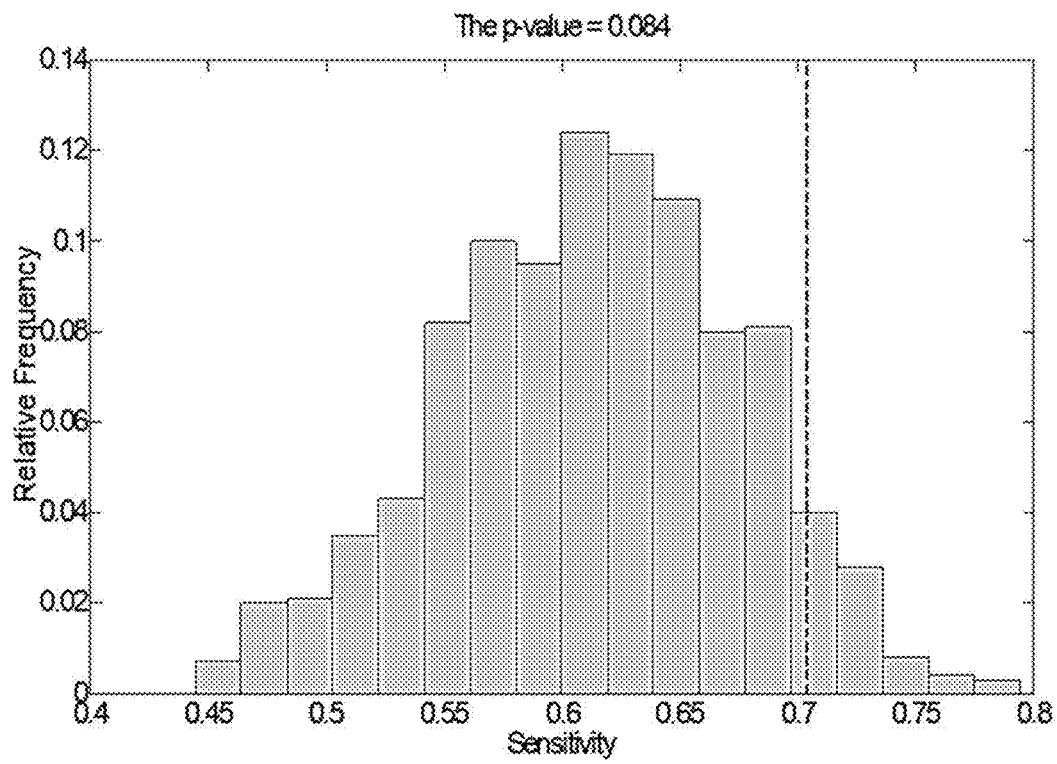
FIG. 5F illustrates the performance comparisons of a trial.
Figure 6A:
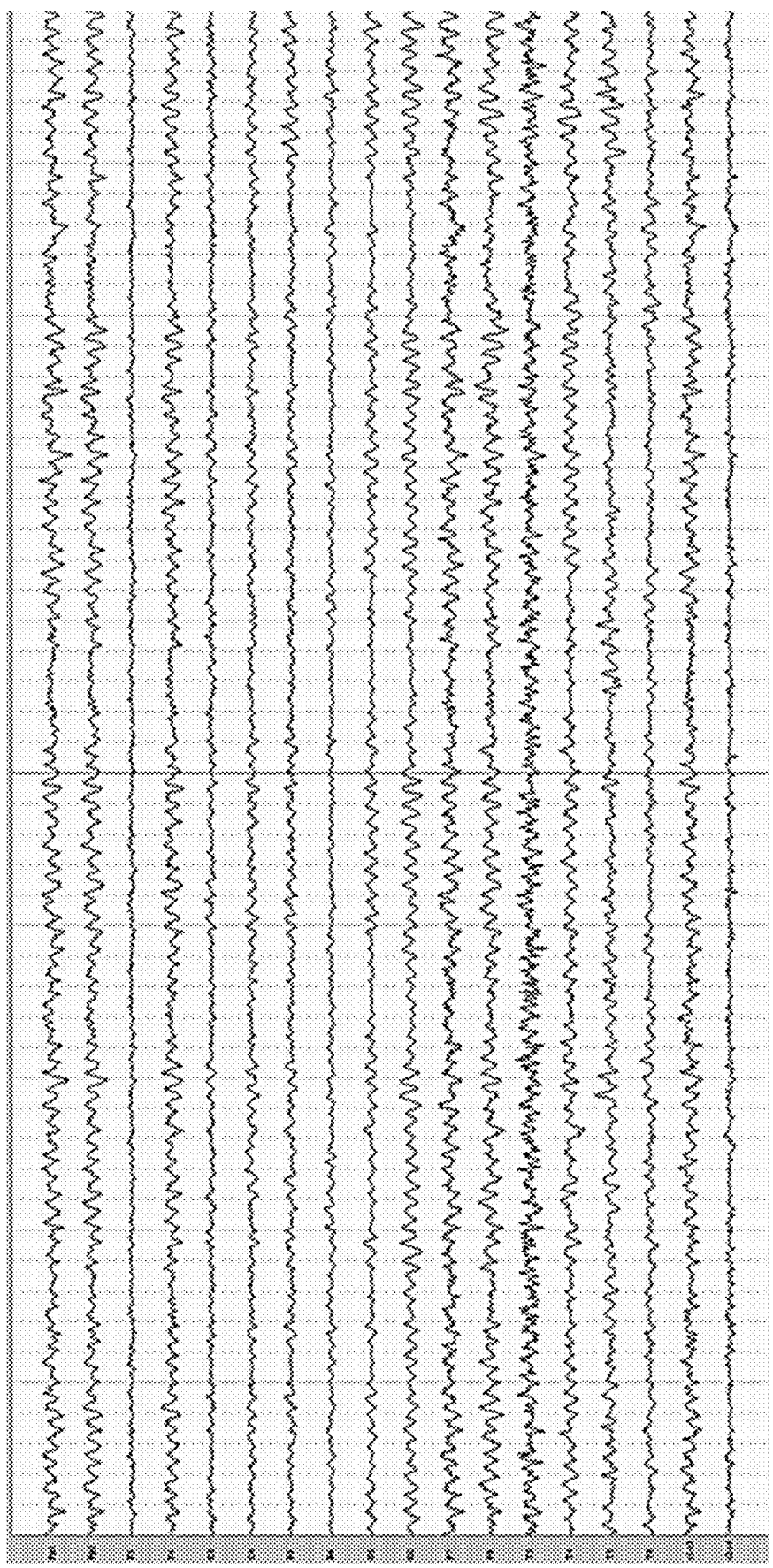
FIGS. 6A and 6B illustrate eye-closed awake and relaxed state EEG signals of a patient having CPS and a patient having PNES.
Figure 6B:
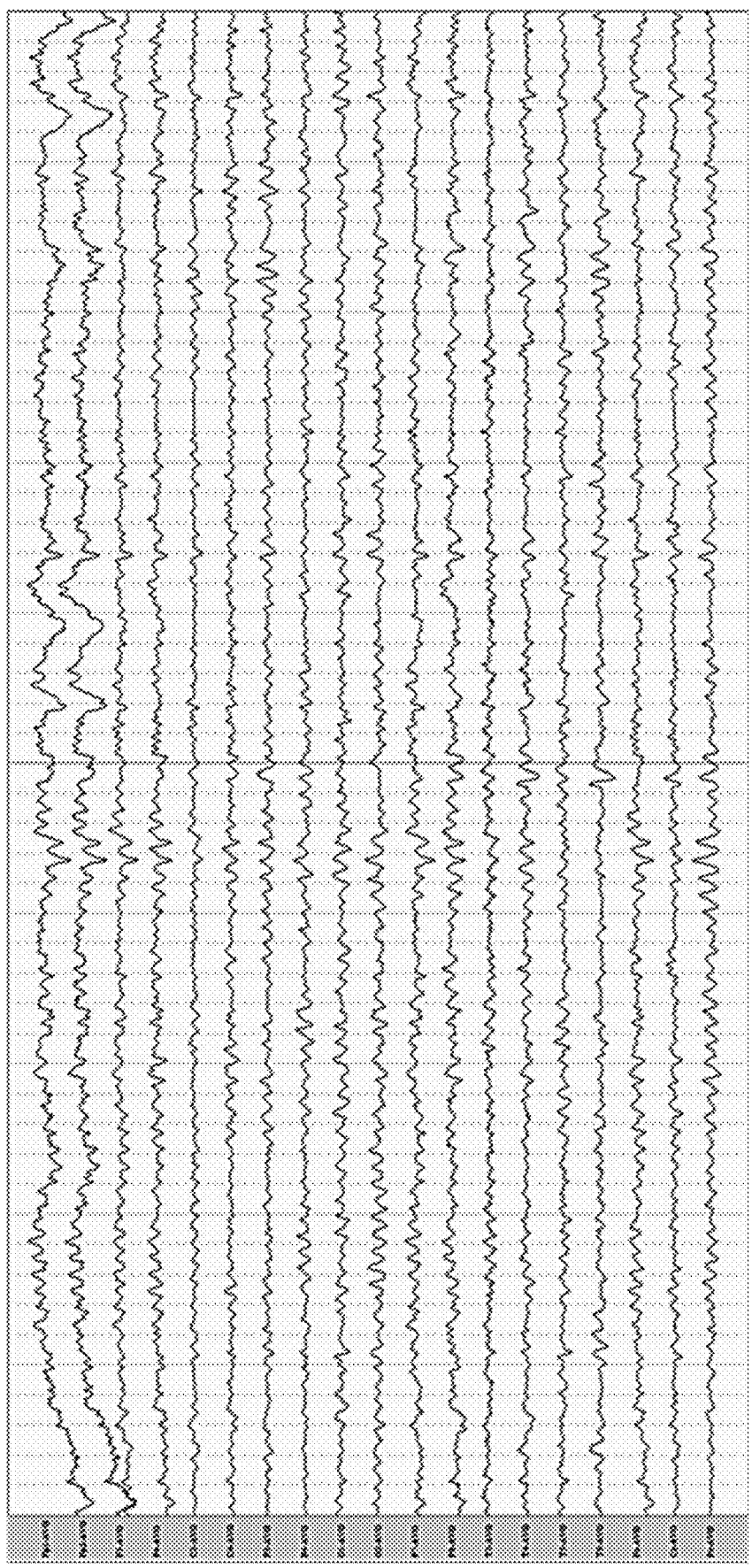
Figure 6C:
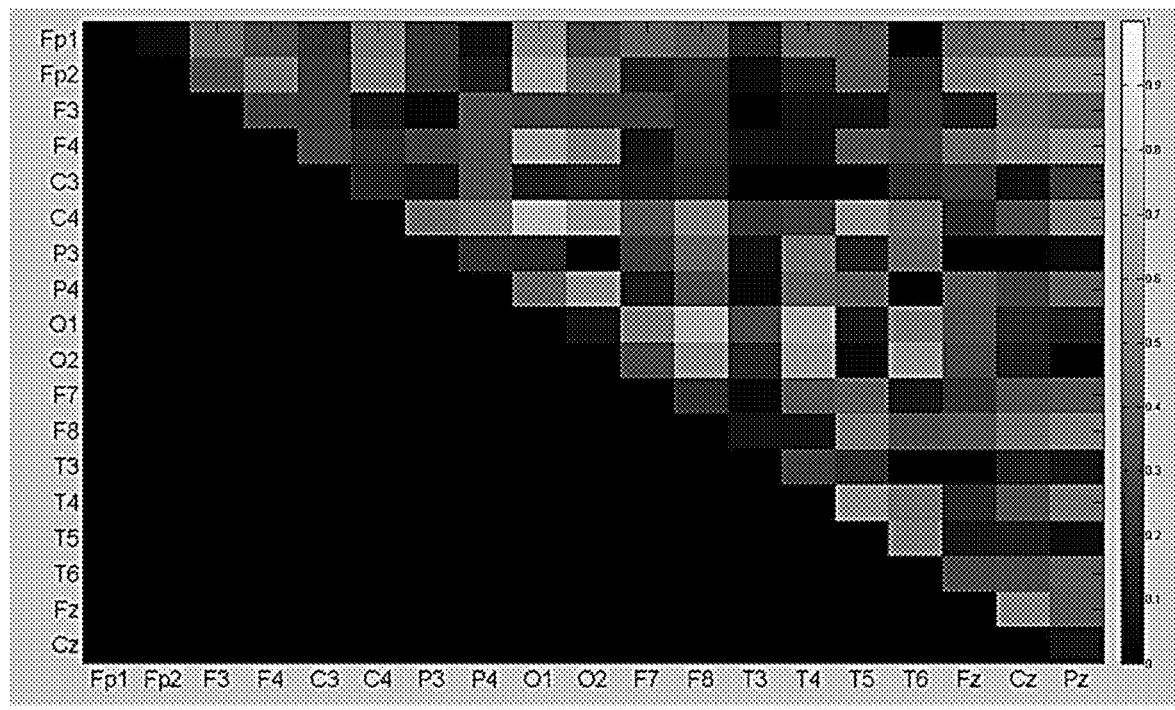
FIG. 6C illustrates a weighted adjacency matrix.
Figure 6D:
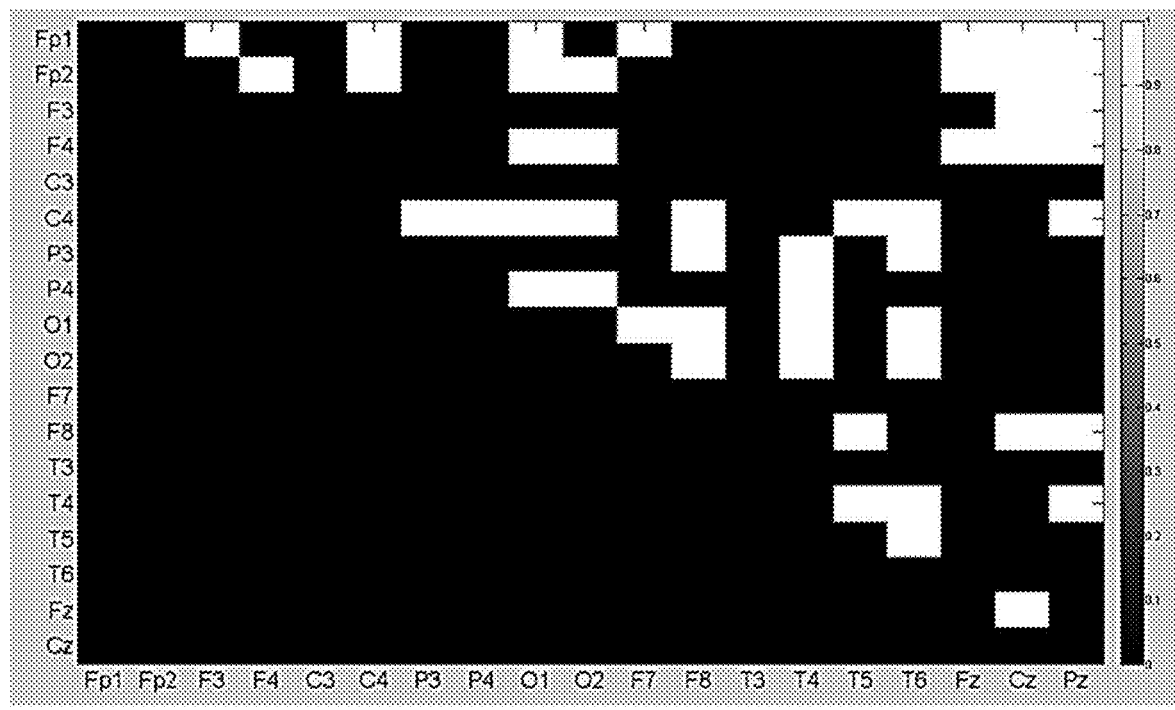
FIG. 6D illustrates an adjacency matrix after applying a threshold on the weighted adjacency matrix in FIG. 6C.
Figure 6E:
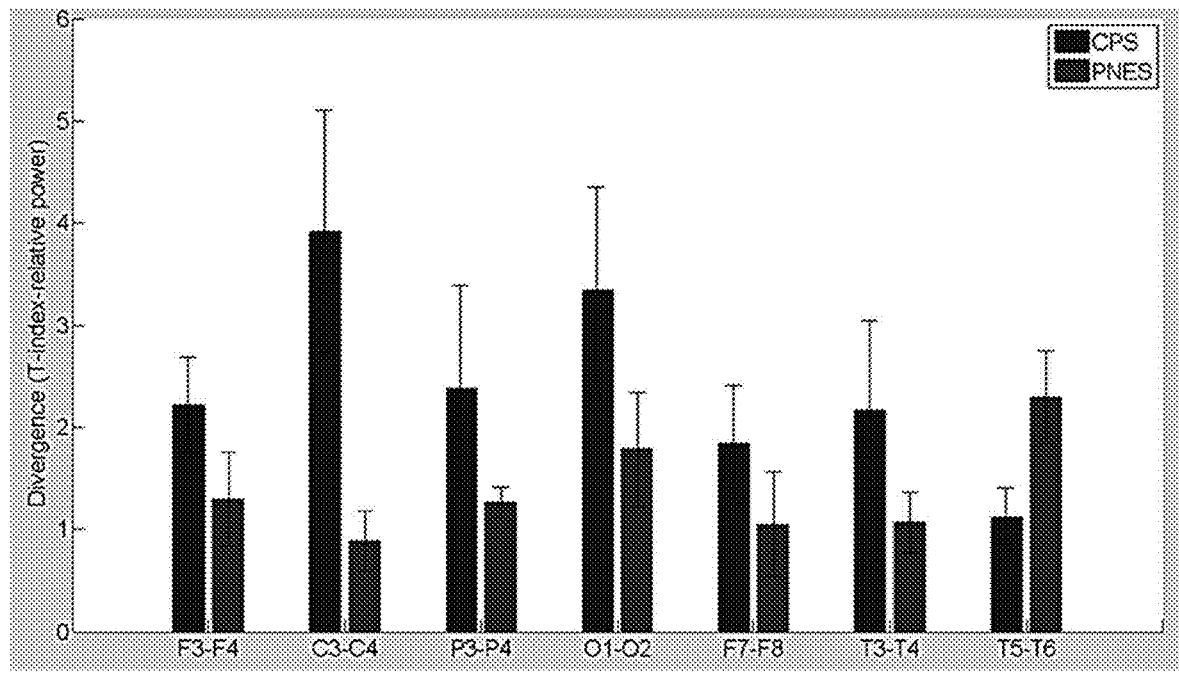
FIGS. 6E-6I illustrate $Tind_{LR}$ of individual anatomically symmetric pairs in the delta frequency band, in the theta frequency band, in the alpha frequency band, in the beta frequency band, and in the gamma frequency band.
Figure 6F:
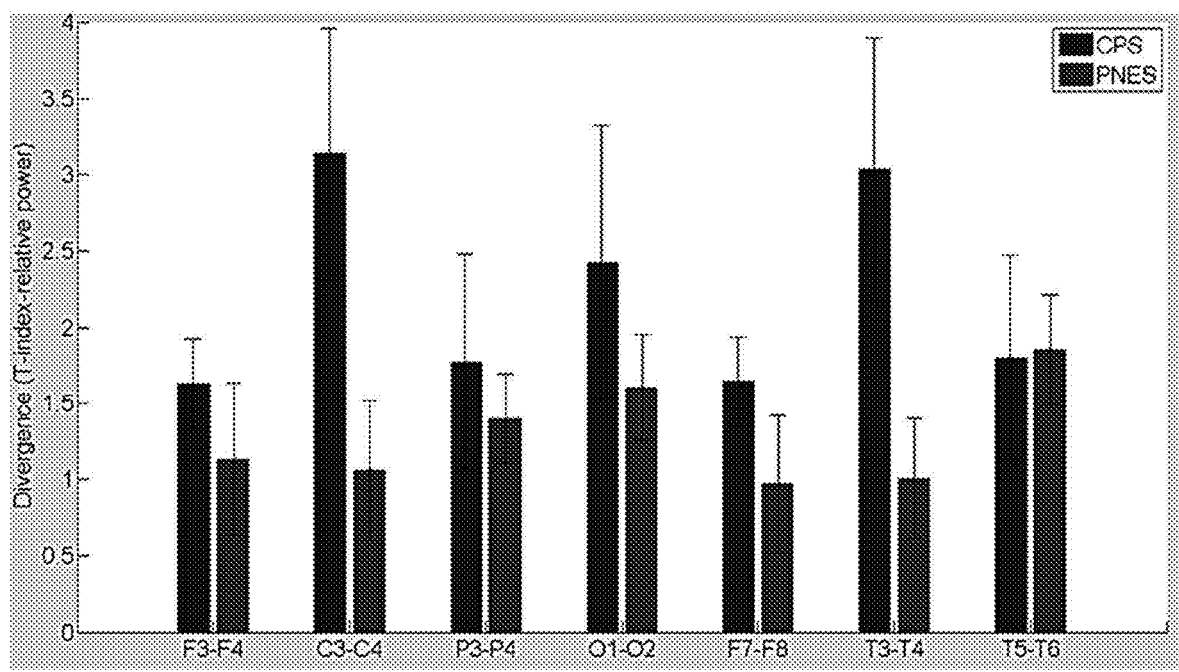
Figure 6G:
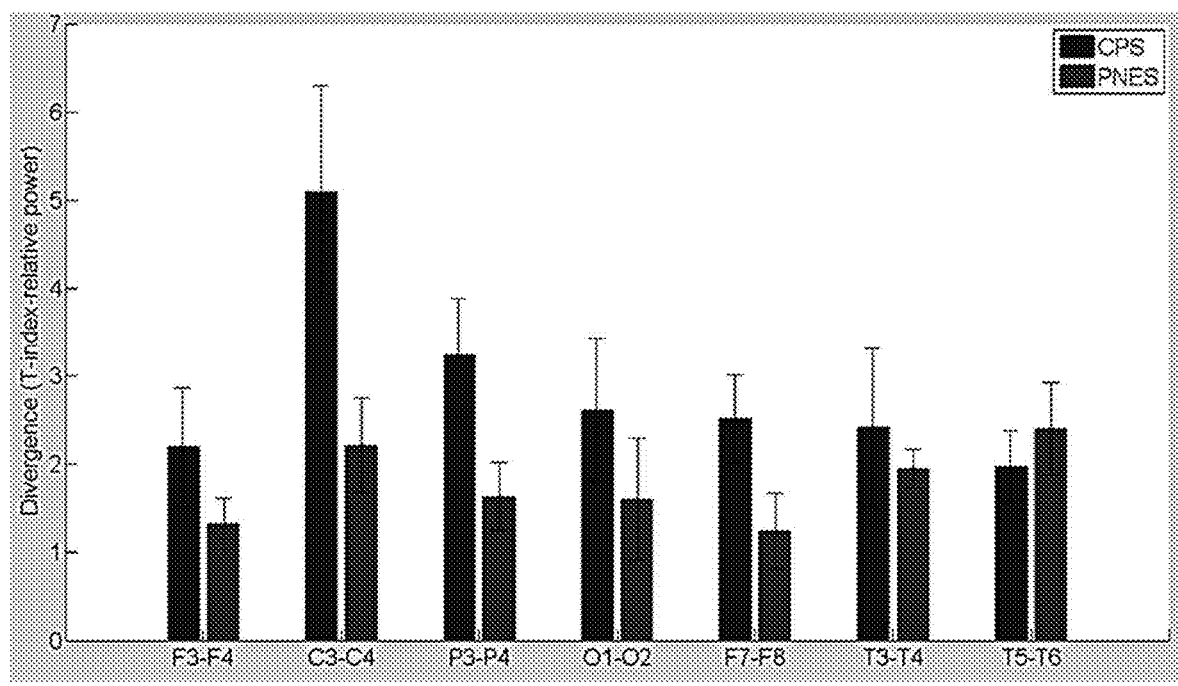
Figure 6H:
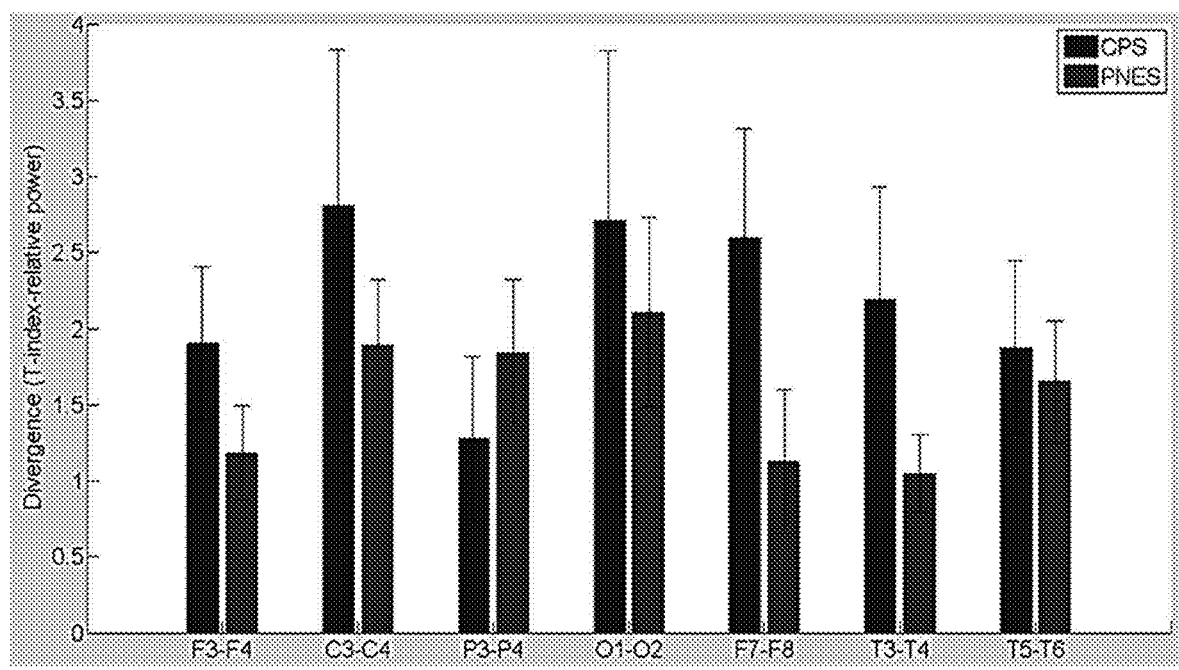
Figure 6I:
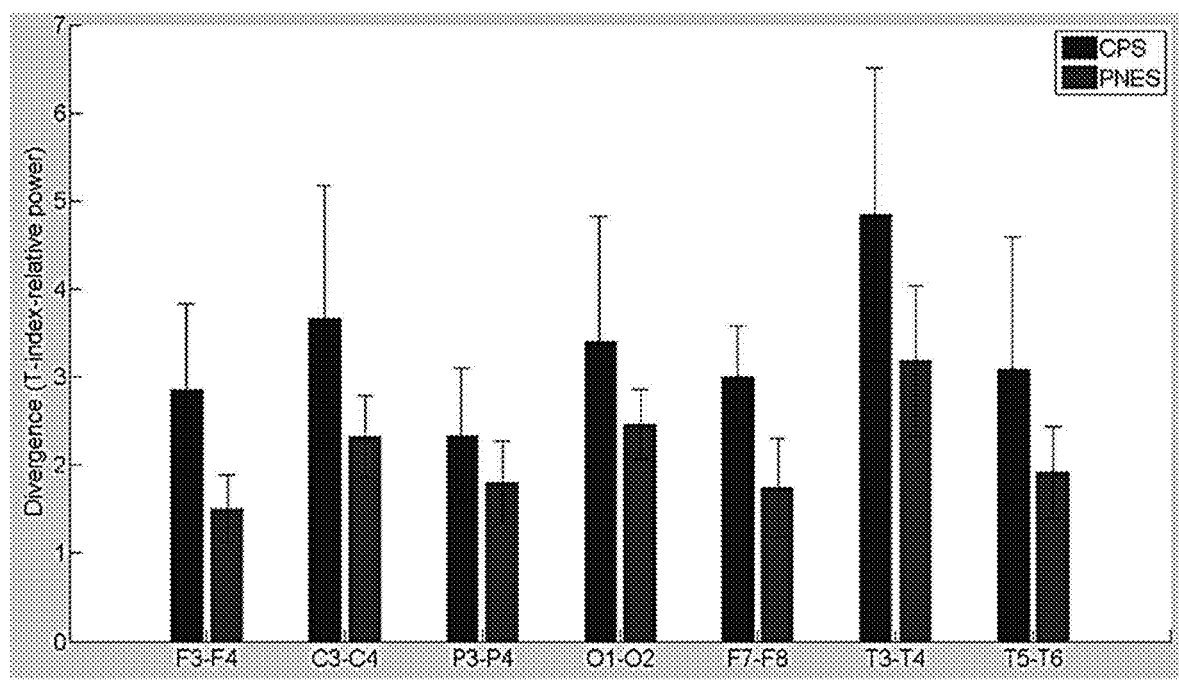
Figure 7A:
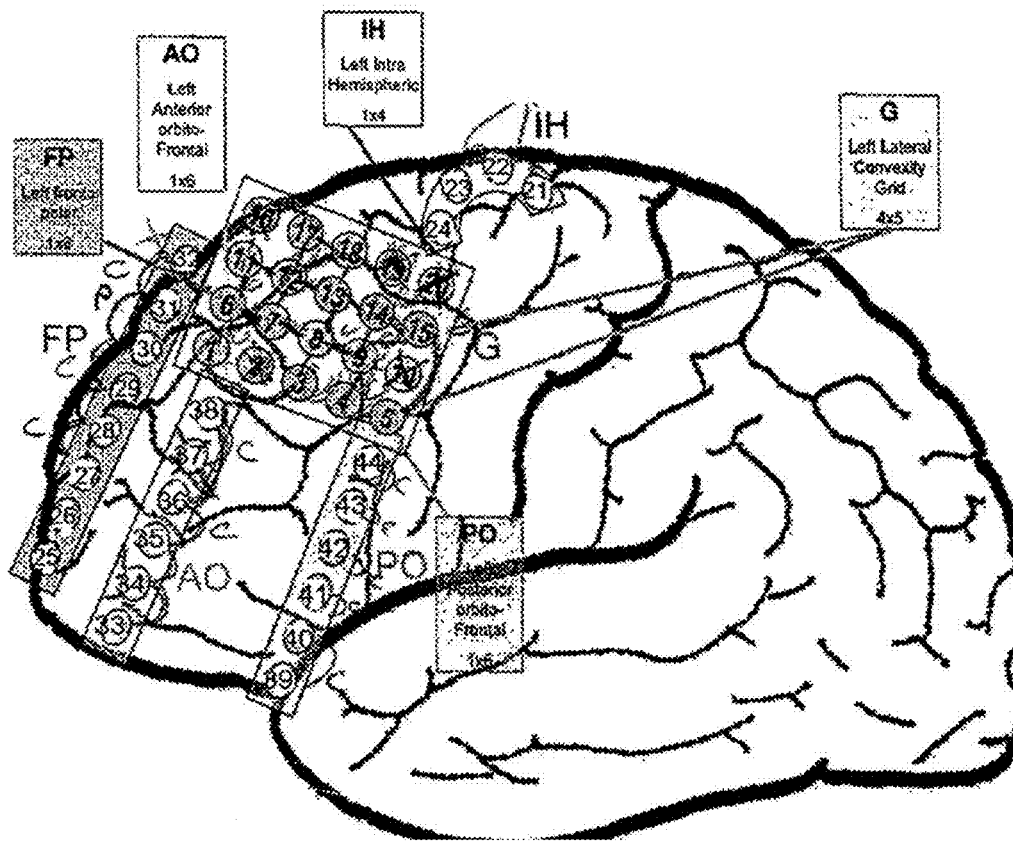
FIG. 7A illustrates electrode placement of the neocortical epilepsy patient.
Figure 7B:
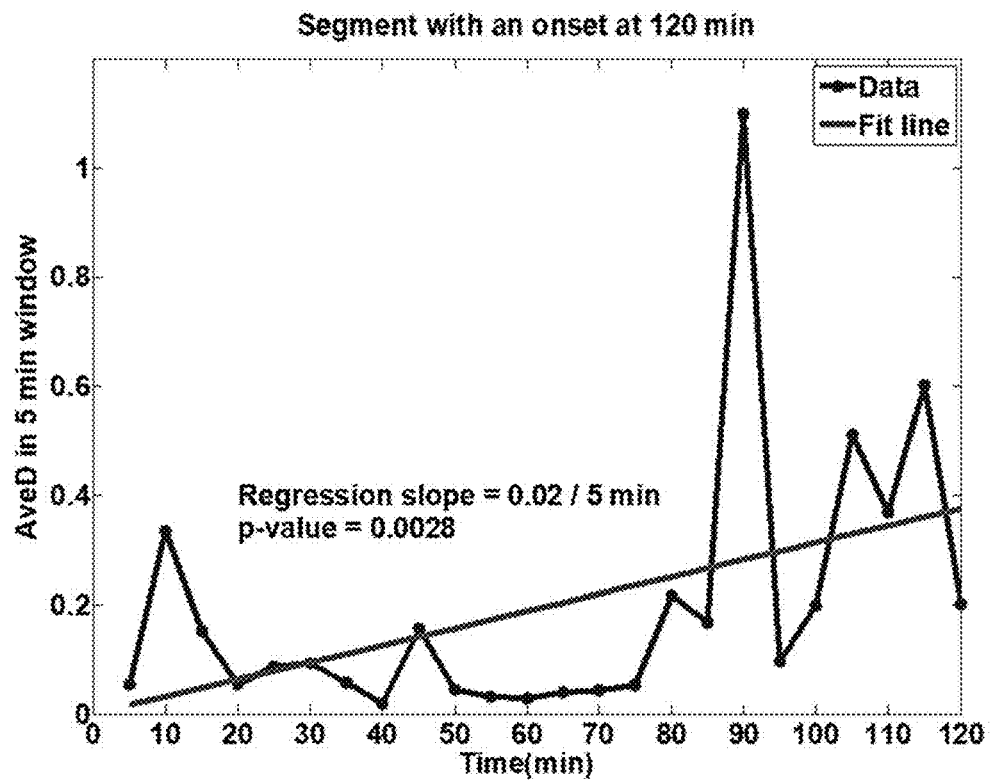
FIGS. 7B and 7C illustrate AveD of the segment with a seizure onset at the 120 minute and without any seizure activity.
Figure 7C:
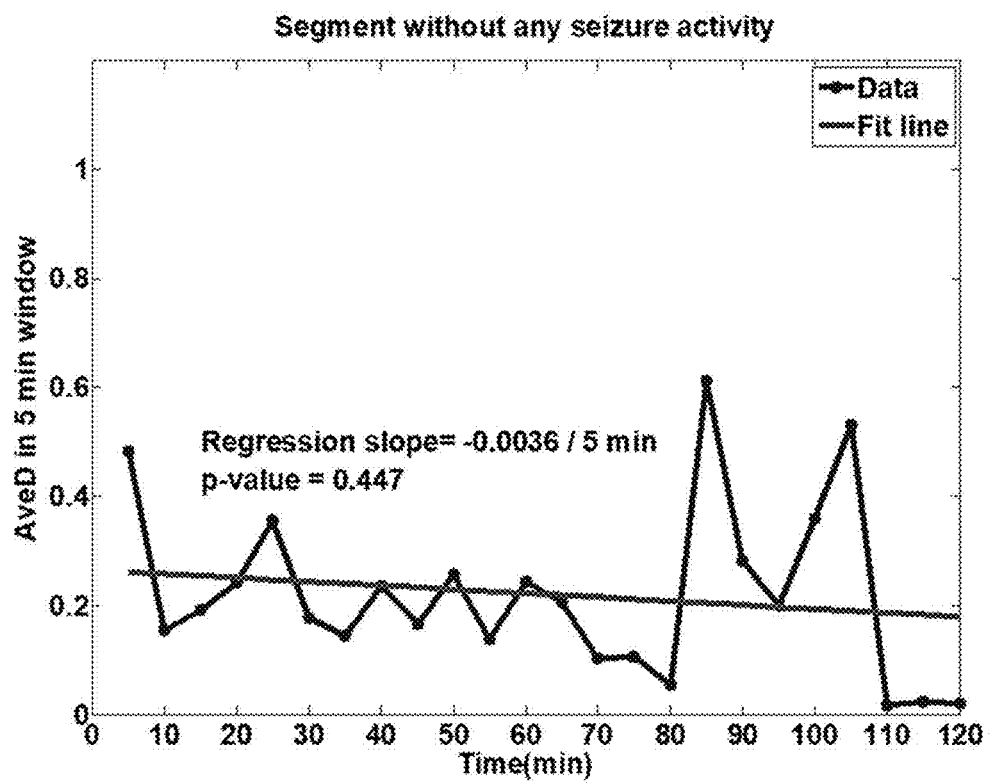
Figure 7D:
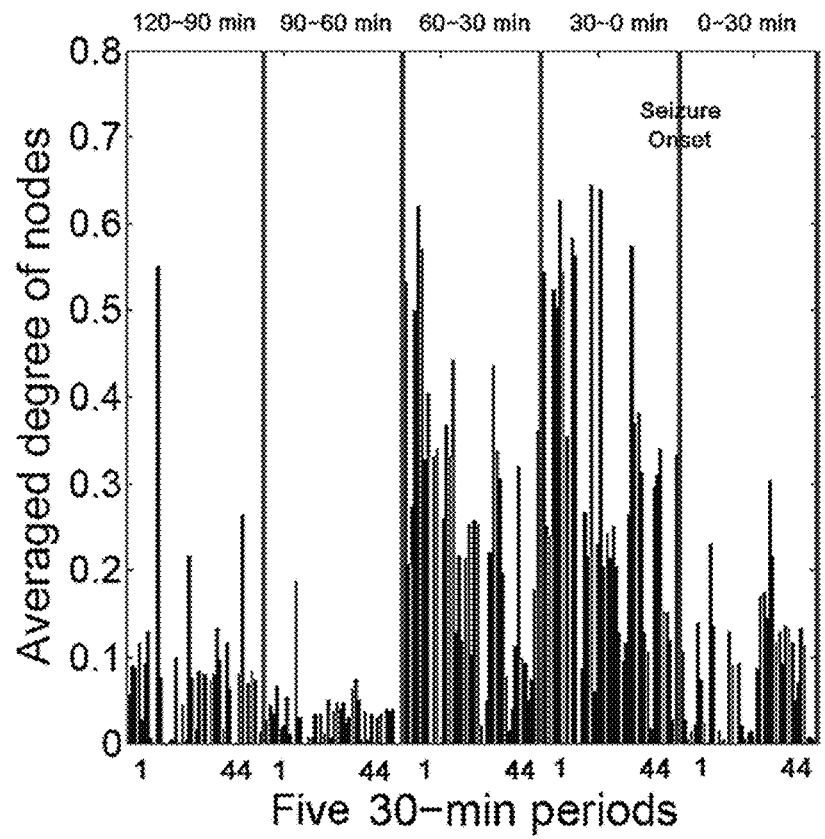
FIG. 7D illustrates averaged degree over 300 calculation windows of nodes in the network.
Figure 7E:
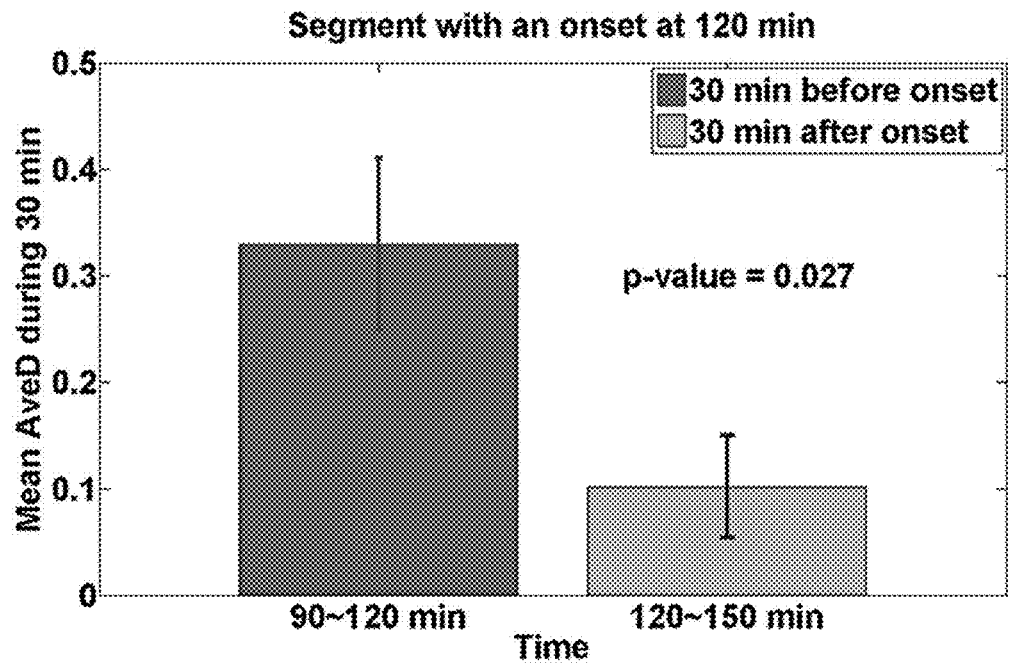
FIGS. 7E and 7F illustrate the average of AveD over 30 minutes before and after a seizure onset and an imaginary seizure onset that is located at 120-minute point.
Figure 7F:
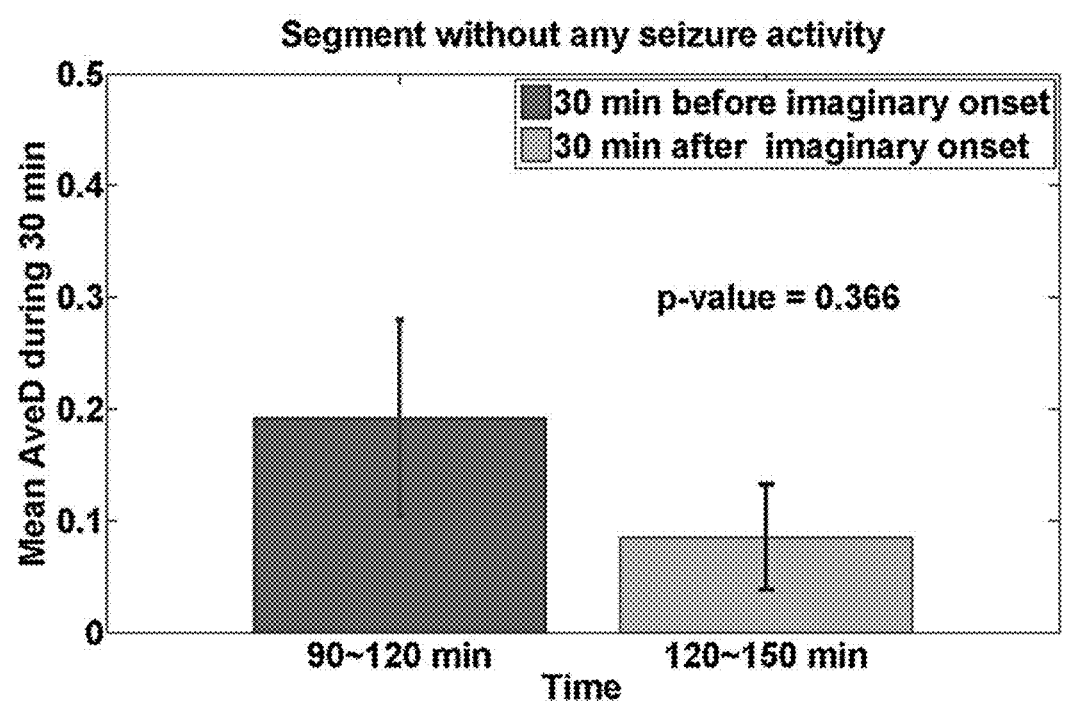

With reference to FIG. 4, shown is a schematic block diagram of a processor system 400 in accordance with various embodiments of the present disclosure. The processor system 400 includes at least one processor circuit, for example, having a processor 403 and a memory 406, both of which are coupled to a local interface 409. To this end, the processor system 400 may comprise, for example, at least one computer or like device. The local interface 409 may comprise, for example, a data bus with an accompanying address/control bus or other bus structure as can be appreciated. In addition, the processor system 400 includes operator interface devices such as, e.g., a display device 412, a keyboard 415, and/or a mouse 418. In some implementations, the operator interface device may be interactive display 421 (e.g., a touch screen) that provides various functionality for operator interaction with the processor system 400. Various sensors such as, e.g., EEG electrodes 424 may also interface with the processor system 400 to allow for acquisition of EEG signals from a subject. In some embodiments, the EEG electrodes 424 may be an array of electrodes configured to be positioned about the subject's head.

Stored in the memory 406 are both data and several components that are executable by the processor 403. In particular, stored in the memory 406 and executable by the processor 403 are various application modules 427 such as, e.g., an electrode application module 103, an EEG recording module 106, a signal conditioning module 109, a signal analysis module 112, and a condition classification module 115 of FIG. 1, and/or other applications. Also stored in the memory 406 may be a data store 430 and other data. In addition, an operating system 433 may be stored in the memory 406 and executable by the processor 403.

It is understood that there may be other applications that are stored in the memory 406 and are executable by the processor 403 as can be appreciated. Where any component discussed herein is implemented in the form of software, any one of a number of programming languages may be employed such as, for example, C, C++, C#, Objective C, Java®, JavaScript®, Perl, PHP, Visual Basic®, Python®, Ruby, Delphi®, Flash®, or other programming languages.

A number of software components are stored in the memory 406 and are executable by the processor 403. In this respect, the term "executable" means a program file that is in a form that can ultimately be run by the processor 403. Examples of executable programs may be, for example, a compiled program that can be translated into machine code in a format that can be loaded into a random access portion of the memory 406 and run by the processor 403, source code that may be expressed in proper format such as object code that is capable of being loaded into a random access portion of the memory 406 and executed by the processor 403, or source code that may be interpreted by another executable program to generate instructions in a random access portion of the memory 406 to be executed by the processor 403, etc. An executable program may be stored in any portion or component of the memory 406 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 406 is defined herein as including both volatile and nonvolatile memory and data storage components. Volatile components are those that do not retain data values upon loss of power. Nonvolatile components are those that retain data upon a loss of power. Thus, the memory 406 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 403 may represent multiple processors 403 and the memory 406 may represent multiple memories 406 that operate in parallel processing circuits, respectively. In such a case, the local interface 409 may be an appropriate network that facilitates communication between any two of the multiple processors 403, between any processor 403 and any of the memories 406, or between any two of the memories 406, etc. The local interface 409 may comprise additional systems designed to coordinate this communication, including, for example, performing load balancing. The processor 403 may be of electrical or of some other available construction.

Although the electrode application module 103, the EEG recording module 106, the signal conditioning module 109, the signal analysis module 112, the condition classification module 115, and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc. Such technologies are generally well known by those skilled in the art and, consequently, are not described in detail herein.

Although the flowcharts of FIGS. 2A-2B and 3A-3B show a specific order of execution, it is understood that the order of execution may differ from that which is depicted. For example, the order of execution of two or more blocks may be scrambled relative to the order shown. Also, two or more blocks shown in succession in FIGS. 2A-2B and 3A-3B may be executed concurrently or with partial concurrence. Further, in some embodiments, one or more of the blocks shown in FIGS. 2A-2B and 3A-3B may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein, including the electrode application module 103, the EEG recording module 106, the signal conditioning module 109, the signal analysis module 112, the condition classification module 115, and/or application(s), that comprises software or code can be embodied in any non-transitory computer-readable medium for use by or in connection with an instruction execution system such as, for example, a processor 403 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

The invention claimed is:

1. A method for cerebral diagnosis for quantitative evaluation and treatment of a subject, comprising:
    obtaining, by processing circuitry, a plurality of electroencephalogram (EEG) signals from a plurality of sensors positioned about a scalp of a subject;
    conditioning, by the processing circuitry, data from the plurality of EEG signals to remove artifacts;
    generating, by the processing circuitry, a cerebral network model based at least in part upon the conditioned EEG signal data, where generating the cerebral network model comprises:
        generating a weighted graph based upon EEG signal features, where the EEG signal features are determined from the conditioned EEG signal data, the weighted graph comprising weights between nodes associated with the conditioned data from the plurality of EEG signals; and
        converting the weighted graph to a binary graph based upon a predefined threshold;
    extracting, by the processing circuitry, network features from the cerebral network model, where extracting the network features comprises:
        determining global network characteristics from the weighted graph or the binary graph of the cerebral network model, where the global network characteristics comprise clustering coefficients and minimum path length, and
    identifying hubs from the nodes of the weighted graph or the binary graph of the cerebral network model, where the hubs are identified based at least in part upon degree of abnormality associated with each node of the weighted graph or the binary graph, path length to contralateral homologous electrode, and connection strength with the contralateral homologous electrode;
    determining, by the processing circuitry, a cerebral condition of the subject based at least in part upon a comparison of the network features and the identified hubs with standard network norms and hubs derived from a test group of individuals of similar age as the subject; and
    outputting, by the processing circuitry, an indication of the cerebral condition of the subject.

2. The method of claim 1, wherein the cerebral condition is based at least in part upon the EEG signal features and the network features.

3. The method of claim 1, wherein the removed artifacts include eye movement artifacts and muscle movement artifacts.

4. The method of claim 1, wherein the removed artifacts include sensor related artifacts.

5. The method of claim 1, wherein determining the cerebral condition of the subject comprises determining an anatomical location of an abnormal condition.

6. The method of claim 1, wherein determining the cerebral condition of the subject comprises determining a severity of an abnormal condition, wherein the severity is based at least in part upon standard deviations from the standard network norms.

7. A method for cerebral diagnosis system operation for quantitative evaluation and treatment of a subject, comprising:
    providing, by a cerebral diagnosis system, procedures to position a plurality of electroencephalogram (EEG) sensors about a scalp of a subject, where the procedures are provided through a user interface of the cerebral diagnosis system, and the procedures comprise a step-by-step application procedure;
    determining a recording condition for each of the plurality of EEG sensors based upon predefined sensor criteria; and
    in response to acceptable recording conditions for the plurality of EEG sensors based upon the predefined sensor criteria:

obtaining, by the cerebral diagnosis system, a plurality of EEG signals from the plurality of EEG sensors by the cerebral diagnosis system;

extracting, by the cerebral diagnosis system, cerebral network features from a cerebral network model, where the cerebral network model that is generated based at least in part upon EEG signal data from the plurality of EEG signals, where extracting the network features comprises:

generating a weighted graph based upon EEG signal features, where the EEG signal features are determined from the EEG signal data, and the weighted graph comprises weights between nodes associated with the EEG signals, determining global network characteristics from the weighted graph or a binary graph converted from the weighted graph, where the global network characteristics comprise clustering coefficients and minimum path length, and identifying hubs from the nodes of the weighted graph or the binary graph of the cerebral network model, where the hubs are identified based at least in part upon degree of abnormality associated with each node of the weighted graph or the binary graph, path length to contralateral homologous electrode, and connection strength with the contralateral homologous electrode;

determining, by the cerebral diagnosis system, a cerebral condition of the subject based at least in part upon a comparison of the network features and the identified hubs with standard network norms and hubs derived from a test group of individuals of similar age as the subject; and providing, by the cerebral diagnosis system, an indication of the cerebral condition of the subject through the user interface.

8. The method of claim 7, wherein the plurality of EEG signals are obtained under subject conditions specified by the cerebral diagnosis system.

9. The method of claim 8, further comprising amplification and filtering of the obtained plurality of EEG signals.

10. The method of claim 8, further comprising sampling the obtained plurality of EEG signals to obtain digital EEG data.

11. The method of claim 10, wherein the digital EEG data is stored in memory.

12. The method of claim 7, wherein:
the weighted graph is generated based upon EEG signal features determined from conditioned EEG signal data; and
the weighted graph is converted to the binary graph based upon a predefined threshold.

13. The method of claim 7, wherein determining the cerebral condition of the subject comprises determining an anatomical location of an abnormal condition.

14. The method of claim 7, wherein determining the cerebral condition of the subject comprises determining a severity of an abnormal condition, wherein the severity is based at least in part upon standard deviations from the standard network norms.

15. A system for cerebral diagnosis for quantitative evaluation and treatment of a subject, comprising:
processing circuitry including a processor and memory having an application that, when executed by the processor, causes the system to:
provide a step-by-step application procedure to position a plurality of sensors about a scalp of a subject;
initiate electroencephalogram (EEG) recording to acquire signals from the plurality of sensors positioned about the scalp of the subject;
condition EEG signal data from the plurality of EEG signals;
determine EEG signal features based at least in part upon the conditioned EEG signal data;
extract cerebral network features from a cerebral network model that is generated based at least in part upon the conditioned EEG signal data, where extracting the cerebral network features comprises:
generating a weighted graph based upon the EEG signal features, the weighted graph comprising weights between nodes associated with the conditioned EEG signal data from the plurality of EEG signals;
converting the weighted graph to a binary graph based upon a predefined threshold; and
determining global network characteristics from the weighted or binary graph of the cerebral network model, wherein the global network characteristics comprise clustering coefficients and minimum path length, and identifying hubs from the nodes of the weighted or binary graph based at least in part upon degree of abnormality associated with each node of the weighted graph or the binary graph, path length to contralateral homologous electrode, and connection strength with the contralateral homologous electrode;
determine a cerebral condition of the subject based at least in part upon a comparison of the cerebral network features and the identified hubs with standard network norms and hubs derived from a test group of individuals of similar age as the subject; and
output an indication of the cerebral condition of the subject.

16. The system of claim 15, wherein execution of the application further causes the system to verify a recording condition of each of the plurality of sensors based upon predefined sensor criteria.

17. The system of claim 15, wherein the conditioning of the EEG signal data comprises removing artifacts associated with movement of the subject from the EEG signal data.

18. The system of claim 15, wherein the cerebral network model is generated based at least in part upon bivariate feature values from the conditioned EEG signal data.

19. The system of claim 15, wherein the condition classification module is configured to identify an anatomical location and severity of an abnormal condition, wherein the severity is based at least in part upon standard deviations from the standard network norms.

* * * * *